(12) United States Patent  
Kadyshevitch et al.

(10) Patent No.: US 7,476,875 B2  
(45) Date of Patent: Jan. 13, 2009

(54) CONTACT OPENING METROLOGY

(75) Inventors: Alexander Kadyshevitch, Hoddieen (IL); Chris Talbot, Emerald Hills, CA (US); Dmitry Shur, Holon (IL); Andreas G. Hegedus, Burlingame, CA (US)

(73) Assignee: Applied Materials, Israel, Ltd., Rehovot (IL)

( * ) Notice: Subject to any disclaimer, the term of this patent is extended or adjusted under 35 U.S.C. 154(b) by 0 days.

(21) Appl. No.: 11/779,224

(22) Filed: Jul. 17, 2007

(65) Prior Publication Data

US 2007/0257191 A1  Nov. 8, 2007

Related U.S. Application Data

(60) Division of application No. 11/181,659, filed on Jul. 13, 2005, now Pat. No. 7,279,689, which is a division of application No. 10/434,977, filed on May 9, 2003, now Pat. No. 7,038,224, which is a continuation-in-part of application No. 10/209,087, filed on Jul. 30, 2002, now Pat. No. 7,078,690.

(51) Int. Cl.  
    H01J 49/00    (2006.01)  
    A61N 5/00     (2006.01)  
(52) U.S. Cl. .............. 250/492.1; 250/310; 250/492.22; 324/751; 324/522; 324/752  
(58) Field of Classification Search ............... None  
    See application file for complete search history.

(56) References Cited

U.S. PATENT DOCUMENTS

| 4,578,279 | A |   | 3/1986 | Zingher |
| 4,843,330 | A | * | 6/1989 | Golladay et al. ............ 324/751 |
| 4,902,964 | A |   | 2/1990 | Szabela et al. |
| 4,902,967 | A |   | 2/1990 | Flesner et al. |
| 5,150,185 | A |   | 9/1992 | Yamada |

(Continued)

FOREIGN PATENT DOCUMENTS

JP      11087451      3/1999

(Continued)

OTHER PUBLICATIONS

International Search Report and Written Opinion for PCT/US2004/014450, Sep. 28, 2004.

(Continued)

*Primary Examiner*—David A. Vanore  
(74) *Attorney, Agent, or Firm*—Tarek N. Fahmi

(57) ABSTRACT

A method for process monitoring includes receiving a sample having a first layer that is at least partially conductive and a second layer formed over the first layer, following production of contact openings in the second layer by an etch process, the contact openings including a plurality of test openings having different, respective transverse dimensions. A beam of charged particles is directed to irradiate the test openings. In response to the beam, at least one of a specimen current flowing through the first layer and a total yield of electrons emitted from a surface of the sample is measured, thus producing an etch indicator signal. The etch indicator signal is analyzed as a function of the transverse dimensions of the test openings so as to assess a characteristic of the etch process.

15 Claims, 14 Drawing Sheets

U.S. PATENT DOCUMENTS

| | | | |
|---|---|---|---|
| 5,637,186 | A | 6/1997 | Liu et al. |
| 5,736,863 | A | 4/1998 | Liu |
| 5,897,710 | A | 4/1999 | Sato et al. |
| 5,903,011 | A | 5/1999 | Hatanaka |
| 6,232,787 | B1 | 5/2001 | Lo et al. |
| 6,235,634 | B1 | 5/2001 | White et al. |
| 6,236,222 | B1 | 5/2001 | Sur, Jr. et al. |
| 6,407,386 | B1 | 6/2002 | Dotan et al. |
| 6,410,353 | B1 | 6/2002 | Tsai |
| 6,504,393 | B1 | 1/2003 | Lo et al. |
| 6,559,662 | B1 | 5/2003 | Yamada et al. |
| 6,614,244 | B2 | 9/2003 | Yamada et al. |
| 6,768,324 | B1 | 7/2004 | Yamada et al. |
| 6,897,440 | B1 | 5/2005 | Yamada |
| 7,038,224 | B2 | 5/2006 | Kadyshevitch et al. |
| 2001/0022345 | A1 | 9/2001 | Isimoto |
| 2002/0070738 | A1 | 6/2002 | Yamada |
| 2002/0093350 | A1 | 7/2002 | Yamada |
| 2002/0134936 | A1 | 9/2002 | Miyako et al. |
| 2003/0104639 | A1 | 6/2003 | Kikuchi et al. |

FOREIGN PATENT DOCUMENTS

| | | |
|---|---|---|
| JP | 2000174077 | 6/2000 |
| JP | 144155 | 5/2001 |
| JP | 2001338956 | 7/2001 |
| JP | 2002083849 | 3/2002 |
| JP | 2002231780 | 8/2002 |
| WO | WO 0180304 A2 | 10/2001 |
| WO | WO 03067653 A2 | 8/2003 |

OTHER PUBLICATIONS

Yacobi et al., "Microanalysis of Solids", 1994 Plenum Press, New York, Chapters 1,2 & 4.
Model EKF-1000 Omnicron Nanotechnology GmbH, Taunusstein, Germany, Available at http://www.omnicron.de/products/ekf1000, 2002.
Yacobi et al., "Scanning Electron Microscopy (Chapter 2)", Microanalysis of Solids, Plenum Press, New York, 1994.
Yamada, Keizo, In-Line Contact and Via Hole Monitoring Method Used Electron-Beam-Induced Substrate Current (EB Scope), NEC Research and Development, Nippon Electric Ltd., Tokyo, Japan, vol. 41, No. 4, Oct. 2000, pp. 336-340, XP000967723, ISSN: 0547-051X.
Invitation to Pay Additional Fees, International Patent Application No. PCT/US03/03494, Applied Materials, Inc., Aug. 19, 2003.
International Search Report, International Patent Application No. PCT/US03/03494, Applied Materials, Inc., Nov. 28, 2003.
Written Opinion, International Patent Application No. PCT/US03/03494, Applied Materials, Inc., Applied Materials, Inc., Jan. 27, 2005.
International Preliminary Examination Report, International Patent Application No. PCT/US03/03494, Applied Materials, Inc., Aug. 19, 2003.
Yamada et al, :An In-Line Contact and Via Hole Inspection Method Using Electron Beam Compensation Current, IEEE, 1999.
Office Action dated May 21, 2004, from U.S. Appl. No. 10/209,087 (filed Jul. 30, 2002), 6 pages.
Response to Office Action filed Jul. 21, 2004, from U.S. Appl. No. 10/209,087 (filed Jul. 30, 2002), 6 pages.
Office Action dated Oct. 19, 2004, from U.S. Appl. No. 10/209,087 (filed Jul. 30, 2002), 4 pages.
Response to Office Action filed Nov. 22, 2004, from U.S. Appl. No. 10/209,087 (filed Jul. 30, 2002), 5 pages.
Notice of Non-Compliant Amendment dated Dec. 23, 2004, from U.S. Appl. No. 10/209,087 (filed Jul. 30, 2002), 2 pages.
Response to Notice of Non-Compliant Amendment filed Feb. 1, 2005, from U.S. Appl. No. 10/209,087 (filed Jul. 30, 2002), 6 pages.
Office Action dated Mar. 2, 2005, from U.S. Appl. No. 10/209,087 (filed Jul. 30, 2002), 10 pages.
Response to Office Action filed Jun. 30, 2005, from U.S. Appl. No. 10/209,087 (filed Jul. 30, 2002), 15 pages.
Office Action dated Nov. 4, 2004, from U.S. Appl. No. 10/434,977 (filed May 9, 2003), 6 pages.
Response to Office Action filed Jan. 4, 2005, from U.S. Appl. No. 10/434,977 (filed May 9, 2003), 15 pages.
Office Action dated May 25, 2006, from U.S. Appl. No. 11/051,339 (filed Feb. 3, 2005), 8 pages.
Response to Office Action filed Sep. 25, 2006, from U.S. Appl. No. 11/051,339 (filed Feb. 3, 2005), 10 pages.
Office Action dated Nov. 24, 2006, from U.S. Appl. No. 11/051,339 (filed Feb. 3, 2005), 6 pages.
Response to Office Action filed Mar. 27, 2007, from U.S. Appl. No. 11/051,339 (filed Feb. 3, 2005), 3 pages.
Office Action dated Jul. 16, 2007, from U.S. Appl. No. 11/051,339 (filed Feb. 3, 2005), 6 pages.
Response to Office Action filed Oct. 2, 2007, from U.S. Appl. No. 11/051,339 (filed Feb. 3, 2005), 15 pages.
Office Action dated Jun. 12, 2006, from U.S. Appl. No. 11/181,659 (filed Jul. 13, 2005), 5 pages.
Response to Office Action filed Jul. 12, 2006, from U.S. Appl. No. 11/181,659 (filed Jul. 13, 2005), 6 pages.
Office Action dated Aug. 16, 2006, from U.S. Appl. No. 11/181,659 (filed Jul. 13, 2005), 8 pages.
Response to Office Action filed Nov. 16, 2006, from U.S. Appl. No. 11/181,659 (filed Jul. 13, 2005), 6 pages.
Office Action dated Jan. 26, 2007, from U.S. Appl. No. 11/181,659 (filed Jul. 13, 2005), 5 pages.
Response to Office Action filed Apr. 17, 2007, U.S. Appl. No. 11/181,659 (filed Jul. 13, 2005), 8 pages.
Office Action dated Mar. 14, 2005, from U.S. Appl. No. 10/695620 (filed Oct. 27, 2003).
Response to Office Action filed Jul. 12, 2005, from U.S. Appl. No. 10/695,620 (filed Oct. 27, 2003), 14 pages.
Office Action dated Jul. 26, 2005, from U.S. Appl. No. 10/695,620 (filed Oct. 27, 2003), 23 pages.
Response to Office Action filed Oct. 18, 2005, from U.S. Appl. No. 10/695,620 (filed Oct. 27, 2003), 11 pages.
Office Action dated Dec. 16, 2005, from U.S. Appl. No. 10/695,620 (filed Oct. 27, 2003), 7 pages.
Response to Office Action filed Mar. 21, 2006, from U.S. Appl. No. 10/695,620 (filed Oct. 27, 2003), 3 pages.
Notice of Non-Compliant Amendment dated Apr. 7, 2006, from U.S. Appl. No. 10/695,620 (filed Oct. 27, 2003), 2 pages.
Respone to Notice of Non Compliant Amendment filed Jun. 6, 2006, from U.S. Appl. No. 10/695,620 (filed Oct. 27, 2003), 3 pages.
Office Action dated Aug. 9, 2006, from U.S. Appl. No. 10/695,620 (filed Oct. 27, 2003), 5 pages.
Response to Office Action filed Sep. 7, 2006 from U.S. Appl. No. 10/695,620 (filed Oct. 27, 2003), 7 pages.
Office Action dated Oct. 25, 2006, from U.S. Appl. No. 10/695,620 (filed Oct. 27, 2003), 6 pages.
Response to Office Action filed Feb. 26, 2007, from U.S. Appl. No. 10/695,620 (filed Oct. 27, 2003), 8 pages.
Office Action dated Apr. 13, 2007, U.S. Appl. No. 10/695,620 (filed Oct. 27, 2003), 7 pages.
Response to Office Action filed Aug. 13, 2007, from U.S. Appl. No. 10/695,620 (filed Oct. 27, 2003), 8 pages.
Office Action dated Sep. 24, 2007, from U.S. Appl. No. 10/695,620 (filed Oct. 27, 2003), 7 pages.
Response to Office Action filed Mar. 21, 2008, from U.S. Appl. No. 10/695,620 (filed Oct. 27, 2003), 8 pages.
Office Action dated Jun. 3, 2008, from U.S. Appl. No. 10/695,620 (filed Oct. 27, 2003), 4 pages.
Response to Office Action filed Aug. 4, 2008, from U.S. Appl. No. 10/695,620 (filed Oct. 27, 2003), 4 pages.
Office Action dated Aug. 25, 2006, from Chinese Patent Application No. 03803196.5 (filed Feb. 14, 2003), 15 pages (translated).
Response to Office Action dated Nov. 29, 2006, from Chinese Patent Application No. 03803196.5 (filed Feb. 14, 2003), 8 pages.
Office Action dated Feb. 16, 2007, from Chinese Patent Application No. 03803196.5 (filed Feb. 14, 2003), 12 pages (translated).
Response to Office Action dated Apr. 12, 2007, from Chinese Patent Application No. 03803196.5 (filed Feb. 14, 2003), 2 pages.

Office Action dated Jul. 6, 2007, from Chinese Patent Application No. 03803196.5 (filed Feb. 14, 2003), 6 pages (translated).

Reponse to Office Action dated Sep. 4, 2007, from Chinese Patent Application No. 03803196.5 (filed Feb. 14, 2003), 3 pages.

International Business Machines, "Non Mechanical Probed Test Element Group (TEG)", Research Disclosure, Mason Publications, Hampshire, GB, vol. 425, No. 76, Sep. 1999, XP007124822, ISSN: 0374-4353.

Invitation to Pay Additional Fees, International Patent Application No. PCT/US03/03494, Applied Materials, Inc., Sep. 12, 2005.

Yamada, et al., An In Line Process Monitoring Method Using Electron Beam Induced Substrate Current, Microelectronics-Reliability, Mar. 2001, pp. 455-459.

* cited by examiner

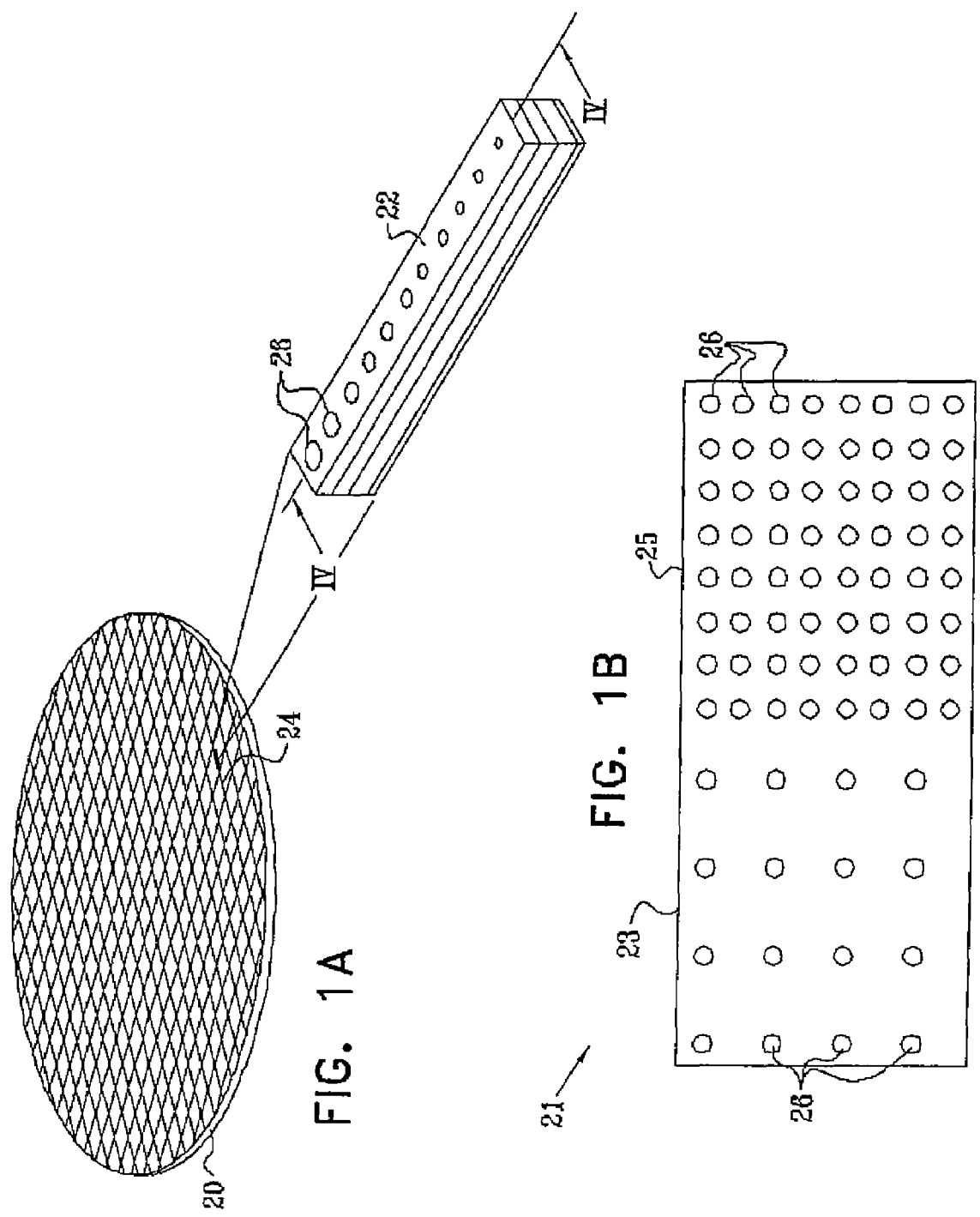

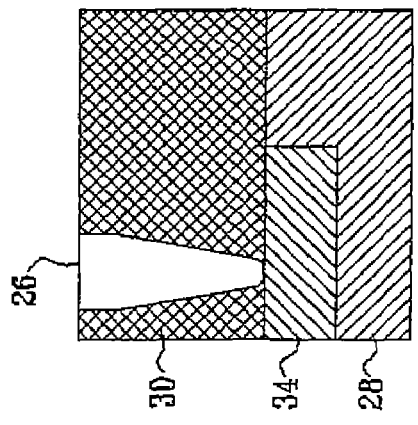
FIG. 2A
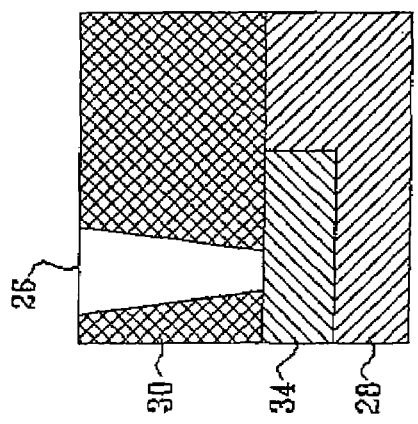
FIG. 2B
FIG. 2C
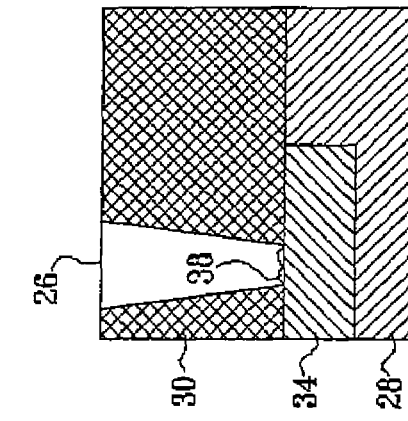
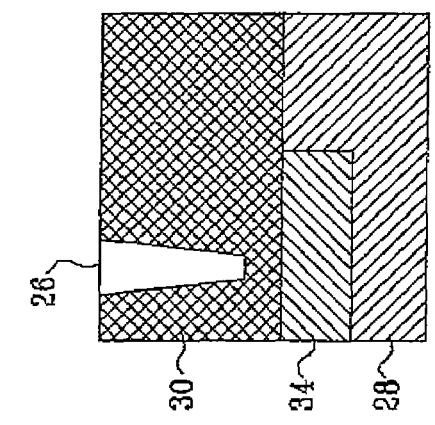
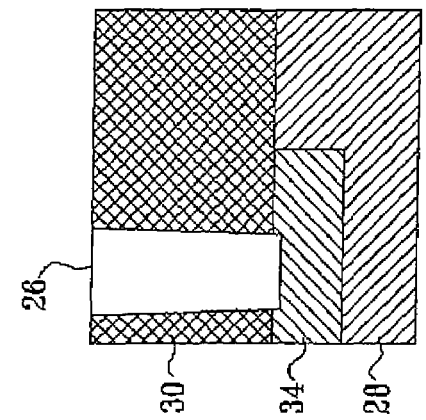
FIG. 2D
FIG. 2E

CONTACT OPENING METROLOGY

CROSS-REFERENCE TO RELATED APPLICATIONS

This application is a divisional of U.S. patent application Ser. No. 11/181,659 filed Jul. 13, 2005 now U.S. Pat. No. 7,279,689 which is a divisional of U.S. patent application Ser. No. 10/434,977, filed May 9, 2003, now U.S. Pat. No. 7,038,224 which is a continuation-in-part of U.S. patent application Ser. No. 10/209,087, filed Jul. 30, 2002, now U.S. Pat. No. 7,078,690 which is assigned to the assignee of the present patent application and is incorporated herein by reference.

FIELD OF THE INVENTION

The present invention relates generally to microfabrication of holes and trenches, including vias, damascene structures and the like, in semiconductor device manufacturing, and specifically to monitoring of contact holes produced on semiconductor wafers.

BACKGROUND OF THE INVENTION

Contact hole production is a common step in semiconductor integrated circuit manufacturing. The contact holes are typically used to make electrical connections to a semiconductor or metal layer through an overlying non-conducting (dielectric) layer, such as an oxide layer, or partially-conductive layer. In order to produce contact holes, a layer of photoresist is deposited on the wafer surface. The photoresist is exposed to ultraviolet or other radiation, hardened and developed in order to form a "mask" over the wafer, with openings at the locations of the contact holes. Then the wafer is transferred to an etch station to form the contact holes through the non-conducting layer down to the semiconductor layer. The photoresist mask is then removed, and the contact holes are filled with metal. A similar process is used in producing trenches or vias in the wafer surface.

In order to ensure consistent device performance, the depth, width and bottom surface cleanliness of contact openings must be carefully controlled. (In the context of the present patent application and in the claims, the term "contact openings" refers to all structures of the type described above, including both contact holes, vias and trenches. Certain techniques for inspecting contact openings and monitoring their production, however, are described by way of example with specific reference to contact holes.) Deviations in the dimensions of contact openings can lead to variations in the contact resistance. These variations can have a serious impact on device performance and can lead to loss of process yield. The manufacturing process must therefore be carefully monitored and controlled, in order to detect deviations in formation of contact openings as soon as they occur and to take corrective action to avoid the loss of costly wafers in process.

It is known in the art to use a scanning electron microscope (SEM) to inspect contact holes and other contact openings. The principles of the SEM and its use in microanalysis of semiconductor device structures are described, for example, by Yacobi et al., in Chapter 2 of *Microanalysis of Solids* (Plenum Press, New York, 1994), which is incorporated herein by reference. Because contact holes are typically much deeper than they are wide, a special high aspect ratio (HAR) imaging mode is used, as described by Yacobi et al. Open contact holes, which reach down through the dielectric layer to the semiconductor below, appear bright in the image, while closed holes, which do not fully expose the semiconductor layer, are dim.

HAR techniques using a SEM are time-consuming and costly to implement, and they become impractical at very high aspect ratios (roughly >10), which are used in some integrated circuits, such as DRAM. They are also not capable of distinguishing between different types of blockage that can cause contact holes to be closed (for example, under-etching of the holes, as opposed to deposition of residues in the bottoms of the holes). Furthermore, HAR imaging techniques can generally be used only after the photoresist mask has been cleaned from the wafer surface. Consequently, there is no possibility of continuing the etching process if it is discovered upon inspection that the contact holes have been underetched.

An alternative method for contact hole inspection is described by Yamada et al., in "An In-Line Process Monitoring Method Using Electron Beam Induced Substrate Current," in *Microelectronics-Reliability* 41:3 (March 2001), pages 455-459, which is incorporated herein by reference. The substrate current in an electron beam system, also known as the specimen current, absorbed current or compensation current, is defined as the absorbed current that flows or would flow from the primary electron beam to ground (earth) via the specimen (i.e., via the wafer). In other words, the specimen current is equal to the difference between the primary beam current (i.e., the current of electrons in the electron beam that irradiates the specimen in the system) and the total yield of electrons emitted from the surface of the specimen due to secondary and backscattered electrons (adjusted for any local charging effects or time constants). The specimen current can be either positive or negative, depending on whether the energy of the primary electron beam is in the positive- or negative-charging domain of the specimen. (The phenomena of positive and negative charging by e-beam irradiation are described in the above-mentioned reference by Yacobi et al.) Yamada et al. directed an electron beam at single contact holes and groups of holes in a $SiO_2$ surface layer overlying a silicon substrate, and measured the resultant specimen current. They found that the specimen current was a good indicator of hole-bottom oxide thickness, as well as of the hole diameter.

Yamada et al. describe further aspects of contact hole measurement in U.S. Patent Application Publication No. US 2002/0070738 A1, whose disclosure is incorporated herein by reference. Semiconductor devices are inspected by measuring the specimen current in an area of a sample having no contact holes as a background value, and comparing this value to the current measured in the area of a hole. A current waveform is automatically evaluated in order to determine whether the measurement is indicative of a defect of the device or of manufacturing equipment used in producing the device.

SUMMARY OF THE INVENTION

The present invention provides improved methods and systems for assessing characteristics of contact openings and other openings formed in dielectric or partially-conductive layers on a sample, and particularly for monitoring the quality of contact openings, such as contact holes, as well as vias or trenches, in production of semiconductor devices.

In embodiments of the present invention, a charged particle beam, typically an electron beam, characterized by a primary beam current, is directed to irradiate areas of a sample in which contact openings or other openings are etched. The etch state of the contact openings is determined by measuring an etch indicator signal generated by the sample in response to the electron beam. The etch indicator signal is typically based on the overall specimen current flowing through a single opening or an array of openings in the sample circuit. Alternatively or additionally, the etch indicator signal may be based the total yield of secondary and backscattered electrons emitted from the surface of the sample. The specimen current can be deduced from the difference between the primary beam current and the total electron yield. Although certain embodiments are described hereinbelow with specific reference to specimen current, the principles of these embodiments may generally be adapted to work with etch indicator signals based on the total yield of secondary and backscattered electrons, instead of or in addition to the specimen current.

The "etch state" or "etch quality" of contact openings, as used in the context of the present patent application and in the claims, refers to one or more of a set of characteristics of the contact or other openings. These characteristics generally include the remaining (residual) thickness of any dielectric material at the bottom of the hole, and they may also include the contact, trench or via depth and/or width, the presence or absence of a residue inside the openings, and any punch through an etch stop layer to damage underlying copper in a damascene structure. The measurement of specimen current is indicative of the diameter of the bottom of the contact hole, where contact is made with the underlying layer, unlike HAR SEM imaging, which shows mainly the diameter at the upper end of the contact hole. The diameter of the bottom of the contact hole is a critical dimension, in terms of its effect on the resistance of the contact formed when the hole is filled with metal.

The etch indicator signal may be measured using a narrow particle beam, to irradiate the area of a single contact opening. Alternatively, a group of contact openings may be irradiated simultaneously, typically using a defocused or rastered focused beam, to give an enhanced signal, as described in the above-mentioned U.S. patent application Ser. No. 10/209, 087.

In some embodiments of the present invention, a calibration procedure is used to determine an absolute threshold specimen current for a given, nominal contact hole diameter. The actual specimen current is then measured by irradiating a number of different contact holes of the nominal diameter, distributed over the surface of the sample. If the measured magnitude of the specimen current due to irradiation of the sample in the area of a given contact hole is equal to or greater than the threshold, the contact hole is considered to have been etched sufficiently. If the measured specimen current is significantly less than the threshold, however, the contact hole is considered to be underetched, indicating that a process fault may have occurred.

Another calibration procedure is used to determine a relative threshold for the specimen current. The relative threshold defines a maximal non-uniformity of specimen current measurements, made on the same type of contact hole in different locations on the sample. Variations in the specimen current measured at the different locations that are greater than the threshold are considered to be indicative of a problem in the manufacturing process.

In some embodiments of the present invention, a test structure is formed on the sample, either on a wafer scribe line or in-die, for use in assessing process quality. The test structure can, for example, comprise an array of contact openings of varying transverse dimension, such as contact holes of graduated diameter, with some openings that are wider than the nominal diameter of functional contact holes to be formed on the sample, and others that are narrower. (In the context of the present patent application and in the claims, "transverse" refers to a direction or dimension perpendicular to the depth dimension of a contact opening.) During etching of the sample, the depths of the contact holes will increase at a rate that is roughly proportional to their diameters. When the etch process is adjusted properly, the specimen current measured for the test holes in the vicinity of the nominal diameter or greater should be high, indicating complete etching of the dielectric. The specimen current measured for the small-diameter holes may be markedly lower, indicating incomplete etching of these holes. The test structure thus provides a reading of the variation of etch depth as a function of hole diameter. Changes in this reading may be used to detect incipient process defects such as underetching, before the defects become serious enough to affect the quality of the functional contact holes.

As another example, the test structure may comprise both dense and sparse arrays of contact holes having the same diameter. The etch rate of contact holes often is a function of contact hole density, due to a micro-loading effect when contact holes are closely spaced. Thus, in general, the etch rate is substantially lower in the dense contact hole arrays than in the sparse arrays. The spacing of the contact holes in dense and sparse arrays in the test structure is typically chosen to represent limiting cases of actual contact hole spacing for in-die patterns. Alternatively or additionally, the density of the contact holes can be determined from prior knowledge of the etch process window. Therefore, by measuring the etch indicator signal with respect to contact holes in the dense and sparse arrays, it is possible to detect etch problems that may occur within in-die patterns due to micro-loading.

In further embodiments of the present invention, novel test configurations are used to enhance the strength or sensitivity of the etch indicator signal for a given particle beam current and contact hole size. These test configurations are useful in particular to enhance sensitivity to very thin layers or remaining dielectric at the bottom of the contact hole. In one of these embodiments, the particle beam irradiates the surface of the sample at a non-normal angle, i.e., with at least a slight tilt. As a result, the energetic primary beam strikes the side walls of the contact holes, rather than the bottom. The surface of the sample is negatively precharged, so that secondary electrons emitted from the side walls and upper edge of the contact holes are driven down toward the bottom of the holes. The secondary electrons, however, are substantially less energetic than the electrons in the primary beam. Therefore, the secondary electrons are less able than the primary electrons to penetrate through thin residue layers that may remain at the bottom of the contact holes. As a result, the measurement of specimen current using an angled particle beam can, under some conditions, provide a more sensitive indicator of etch state than can be achieved using a conventional, normal-incidence beam.

The angled beam may be used to enhance the sensitivity of specimen current measurements in other applications, as well, as will be apparent to those skilled in the art. For example, the angled beam may be used to measure punch-through of contact hole side walls, which leads to current leakage through the side walls to nearby polysilicon structures. As another example, contact holes produced at the periphery of a silicon wafer may be tilted due to the effect of fringing fields in the dielectric etch process. The electron beam may be angled so that the electrons still strike the bottom of these tilted contact holes or to ensure the beam hits the contact hole side wall at a desired angle.

In another embodiment, the sample is irradiated simultaneously by a charged particle beam and by electromagnetic radiation, i.e., by a beam of photons, typically a beam of visible, near-infrared or ultraviolet light. This technique is useful, for example, in assessing the etch quality of contact holes used to contact P-N junctions in functional dice (or otherwise connected to P-N junctions), which are fabricated in a semiconductor wafer. When such a junction is biased by charge from a charged particle beam alone, little or no specimen current may flow through to the semiconductor substrate if the charge-induced voltage reverse-biases the junction (since the junction acts as a non-conducting reverse-biased diode). If the junction is irradiated with light at a photon energy greater than the semiconductor bandgap energy, however, electron-hole pairs will be created at the P-N junction and in the substrate, so that a significant specimen current may flow through the P-N junction. The combination of particle beam and electromagnetic irradiation can also be used to measure other aspects of devices produced on semiconductor wafers, particularly front-end device structures, as will be apparent to those skilled in the art.

As noted above, in measurements of specimen current flowing through contact holes, it is frequently advantageous to negatively bias the upper surface of the sample, i.e., the surface on which the electron beam is incident. In systems known in the art, the negative bias is created by operating the electron beam at high energy, in the negative charging domain (i.e., the energy range in which the total yield of backscattered and secondary electrons from the wafer is less than the primary electron beam current), in order to precharge the surface. High-energy irradiation, however, can cause damage to the sample. Therefore in some embodiments of the present invention, an electrode near the surface is used to apply a negative bias potential while the surface is irradiated by the electron beam. The bias potential causes the secondary electrons emitted from the surface to return to the surface, thus creating a net negative precharge, without the need for high-intensity, high-energy irradiation of the surface as in systems known in the art.

There is therefore provided, in accordance with an embodiment of the present invention, a method for process monitoring, including:

receiving a sample having a first layer that is at least partially conductive and a second layer formed over the first layer, following production of contact openings in the second layer by an etch process, the contact openings including a plurality of test openings having different, respective transverse dimensions;

directing a beam of charged particles to irradiate the test openings;

measuring, in response to the beam, at least one of a specimen current flowing through the first layer and a total yield of electrons emitted from a surface of the sample, thus producing an etch indicator signal; and analyzing the etch indicator signal as a function of the transverse dimensions of the test openings so as to assess a characteristic of the etch process.

In an aspect of the invention, analyzing the etch indicator signal includes assessing a residual thickness of the dielectric layer at a bottom of the test openings as a function of the transverse dimensions. In one embodiment, the test openings include a first opening having a first transverse dimension, and at least a second opening having a second transverse dimension that is less than the first transverse dimension, and the method includes controlling the etch process, in response to the etch indicator signal, so that the first opening is sufficiently deep to reach the first layer, while at least the second opening is not sufficiently deep to reach the first layer. In another embodiment, the test openings further include a third opening, having a third transverse dimension intermediate the first and second transverse dimensions, and analyzing the etch indicator signal includes detecting a potential process defect when the etch indicator signal indicates that the third opening is not sufficiently deep to reach the first layer.

In another aspect of the invention, the sample may have a barrier layer formed between the first and second layers, and assessing the residual thickness may include analyzing the etch indicator signal after etching the second layer in order to assess an integrity of the barrier layer, and then analyzing the etch indicator signal after etching the barrier layer, typically in order to verify that at least some of the contact openings have been etched through the barrier layer to the first layer.

In still another aspect of the invention, analyzing the etch indicator signal includes assessing a critical dimension of a bottom of the test openings as a function of the transverse dimensions.

Optionally, analyzing the etch indicator signal includes measuring a beam current of the beam of charged particles, and analyzing a ratio of the etch indicator signal to the beam current. Alternatively, measuring at least one of the specimen current and the total yield includes measuring the total yield of the electrons emitted from the surface of the sample and further includes measuring a primary current of the beam, and taking a difference between the primary current and the total yield to determine the etch indicator signal.

In a disclosed embodiment, the plurality of test openings includes multiple groups of the test openings in respective test areas, which are distributed in different locations across the sample, and directing the beam includes positioning at least one of the beam and the sample so as to irradiate each of at least two of the test areas in turn. Analyzing the etch indicator signal may include evaluating a variation of the etch indicator signal across the sample so as to assess a uniformity of the etch process.

Typically, directing the beam includes operating the beam so as to precharge a surface of the sample in proximity to the test openings, so as to facilitate measurement of the specimen current.

In an aspect of the invention, the sample includes a semiconductor wafer, and the contact openings include at least one of contact holes, trenches and vias. At least some of the contact openings not included in the plurality of test openings may belong to multiple microelectronic circuits on the wafer, wherein the circuits are separated by scribe lines, and the test openings are located on one of the scribe lines.

In another aspect of the invention, receiving the sample includes receiving the sample with a photoresist layer overlying the second layer, the photoresist layer having been used in etching the contact openings, and analyzing the etch indicator signal includes monitoring the etch indicator signal while irradiating the test area, prior to removing the photoresist layer. The method may include, if the etch indicator signal indicates that a residual thickness of the second layer at a bottom of one or more of the test openings is greater than a predetermined limit, further etching the second layer using the photoresist layer so as to increase the depth.

In one embodiment, analyzing the etch indicator signal includes detecting a residue within the contact openings, and the method irradiating the sample with the beam of charged particles so as to remove the residue.

Optionally, directing the beam includes directing a pulsed beam of the charged particles to irradiate the test openings, and measuring at least one of the specimen current and the total yield of electrons includes measuring a time variation of the specimen current by capacitive coupling to the sample.

There is also provided, in accordance with an embodiment of the present invention, a method for process monitoring, including:

receiving a sample having a first layer that is at least partially conductive and a second layer formed over the first layer, following production of contact openings in the second layer by an etch process, the contact openings including at least first and second arrays of test openings, characterized by different, respective first and second spacings between the test openings in the first and second arrays;

directing a beam of charged particles to irradiate the test openings;

measuring, in response to the beam, at least one of a specimen current flowing through the first layer and a total yield of electrons emitted from a surface of the sample, thus producing an etch indicator signal; and analyzing the etch indicator signal as a function of the spacings of the arrays of the test openings so as to assess a characteristic of the etch process.

In an aspect of the invention, analyzing the etch indicator signal includes assessing a residual thickness of the dielectric layer at a bottom of the test openings as a function of the spacings. Typically, the first spacing is substantially greater than the second spacing, and the method includes controlling the etch process, in response to the etch indicator signal, so that the test openings in the first array are sufficiently deep to reach the first layer, while the test openings in the second array are not sufficiently deep to reach the first layer.

There is additionally provided, in accordance with an embodiment of the present invention, a method for monitoring a process carried out on a sample, the method including:

directing a beam of charged particles to irradiate the sample along a beam axis that deviates substantially in angle from a normal to a surface of the sample;

measuring, in response to incidence of the beam on the sample, a specimen current flowing through the sample; and analyzing the specimen current so as to assess a characteristic of the process.

Typically, the sample has a first layer that is at least partially conductive and a second layer formed over the first layer, and the process includes an etch process, which is applied to the sample so as to produce contact openings in the second layer, and directing the beam includes irradiating the contact openings, and analyzing the specimen current includes assessing the etch process. Some of the contact holes may be characterized by a tilt relative to the normal to the surface, and directing the beam may then include angling the beam so as to compensate for the tilt.

Typically, the contact openings have side walls and a bottom, and directing the beam may additionally or alternatively include angling the beam so that more of the charged particles strike the side walls than strike the bottom. In an aspect of the invention, the contact openings are characterized by an aspect ratio, and directing the beam includes aligning the beam axis at an angle that deviates from the normal to the surface by at least an arctangent of an inverse of the aspect ratio.

There is further provided, in accordance with an embodiment of the present invention, a method for process monitoring, including:

directing a beam of charged particles to irradiate a surface of a sample, whereby electrons are emitted from the surface;

applying an electric field in a vicinity of the surface, so as to cause at least a portion of the emitted electrons to return to the surface, thereby generating a negative precharge at the surface; and receiving a signal produced by the sample in response to the beam and the negative precharge.

Typically, the sample has a first layer that is at least partially conductive and a second layer formed over the first layer, and the negative precharge is formed on the surface of the dielectric layer.

In an aspect of the invention, directing the beam includes operating the beam during a precharging interval so as to generate the negative precharge at the surface, and then operating the beam after the precharging interval so as to generate the signal. Typically, operating the beam during the precharging interval includes setting the beam source so that electrons have an energy in a positive charging domain of the surface of the sample.

There is moreover provided, in accordance with an embodiment of the present invention, a method for testing a semiconductor device, including:

irradiating a junction in the semiconductor device with a first beam including electromagnetic radiation;

irradiating the device with a second beam including charged particles, so that at least some of the charged particles are incident on the junction substantially simultaneously with the electromagnetic radiation; and measuring, in response to incidence of the first and second beams on the junction, a property of the device.

In an aspect of the invention, measuring the property includes forming an electronic image of the device.

In another aspect of the invention, the junction includes a semiconductor material, and irradiating the junction with the first beam includes irradiating the junction with photons having an energy greater than or equal to a bandgap of the semiconductor material. Typically, the junction includes a P-N junction.

Additionally or alternatively, measuring the property includes measuring a current flowing through the device, wherein a dielectric layer is formed over the junction, and a contact hole is formed through the dielectric layer in order to contact the junction, and wherein irradiating the junction with the first and second beams includes irradiating an interior of the contact hole, and wherein measuring the current includes assessing a characteristic of the contact hole based on the current. Typically, assessing the characteristic includes assessing a suitability of the contact hole to make a conductive electrical contact with the junction.

There is furthermore provided, in accordance with an embodiment of the present invention, a method for process monitoring, including:

receiving a sample having a first layer that is at least partially conductive and a second layer formed over the first layer, following production of contact openings in the second layer by an etch process;

directing a beam of charged particles to irradiate one or more of the contact openings;

measuring a primary current of the beam and a total yield of electrons emitted from a surface of the sample in response incidence of the beam on the contact openings; and analyzing a relation between the primary current and the total yield of the electrons so as to assess a characteristic of the etch process.

Analyzing the relation may include analyzing a difference between the primary current and the total yield or, additionally or alternatively, analyzing a ratio between the primary current and the total yield.

There is also provided, in accordance with an embodiment of the present invention, a method for process monitoring of a sample having a first layer that is at least partially conductive and a second layer formed over the first layer, wherein contact openings are formed in the second layer by an etch process, the method including:

determining, for a given set of characteristics of the contact openings, a threshold level of an etch indicator signal, which is produced by measuring at least one of a specimen current flowing through the first layer and a total yield of electrons emitted from a surface of the sample in response to irradiation of the contact openings by a beam of charged particles;

directing the beam of charged particles to irradiate each of a plurality of the contact openings that have the given set of characteristics and are disposed at different, respective positions over a surface of the sample;

determining, in response to the beam, the etch indicator signal produced at each of the respective positions of the plurality of the contact openings; and comparing the etch indicator signal produced at the respective positions to the threshold level so as to assess a characteristic of the etch process.

Typically, comparing the etch indicator signal includes determining, if an absolute magnitude of the specimen current falls below the threshold level by more than a predetermined margin, that at least some of the contact openings are underetched.

Additionally or alternatively, determining the threshold level includes finding the level of the etch indicator signal that corresponds to etching of the contact openings through the second layer to expose the first layer within the opening. In a disclosed embodiment, finding the level includes calibrating the threshold level in a procedure performed on a test sample, for subsequent application in assessing the characteristic of the etch process performed on other samples. Typically, calibrating the threshold level includes making measurements of the etch indicator signal generated by the test sample, and comparing the measurements to at least one of a cross-sectional profile of the contact openings in the test sample and a conductivity of electrical contacts made through the contact openings in the test sample.

In an embodiment of the invention, the sample has a barrier layer formed between the first and second layers, and finding the level of the etch indicator signal includes finding a first level that corresponds to etching of the contact openings through the second layer to expose the barrier layer, and finding a second level that corresponds to etching of the contact openings through the barrier layer to expose the first layer within the openings. Typically, comparing the etch indicator signal includes analyzing the etch indicator signal after etching the second layer in order to assess an integrity of the barrier layer, and then analyzing the etch indicator signal after etching the barrier layer in order to verify that at least some of the contact openings have been etched through the barrier layer to the first layer.

The method may include evaluating a variation of the etch indicator signal across the sample so as to assess a uniformity of the etch process, and signaling that a process fault has occurred if the variation of the etch indicator signal across the sample is greater than a predetermined maximum.

There is additionally provided, in accordance with an embodiment of the present invention, a method for process monitoring of a sample having a first layer that is at least partially conductive and a second layer formed over the first layer, wherein contact openings are formed in the second layer by an etch process, the method including:

directing a beam of charged particles to irradiate each of a plurality of the openings that share a given set of characteristics and are disposed at different, respective positions across the sample;

measuring at least one of a specimen current flowing through the first layer and a total yield of electrons emitted from a surface of the sample in response to irradiation of the contact openings by the beam of charged particles, thus producing an etch indicator signal as a function of the respective positions of the plurality of the openings; and evaluating a variation of the etch indicator signal across the sample so as to assess a uniformity of the etch process.

In an aspect of the invention, evaluating the variation includes determining that a process fault has occurred if the variation of the etch indicator signal across the sample is greater than a predetermined maximum.

There is further provided, in accordance with an embodiment of the present invention, apparatus for etching a sample having a first layer that is at least partially conductive and a second layer formed over the first layer, contact openings having been created in the second layer by an etch process, the contact openings including a plurality of test openings having different, respective transverse dimensions, the apparatus including:

a test station, which includes:

a particle beam source, which is adapted to direct a beam of charged particles to irradiate the test openings; and a current measuring device, which is coupled to measure, in response to the beam, at least one of a specimen current flowing through the first layer and a total yield of electrons emitted from a surface of the sample, thus producing an etch indicator signal; and a controller, which is adapted to analyze the etch indicator signal as a function of the transverse dimensions of the test openings so as to assess a characteristic of the etch process.

There is moreover provided, in accordance with an embodiment of the present invention, apparatus for etching a sample having a first layer that is at least partially conductive and a second layer formed over the first layer, contact openings having been created in the second layer by an etch process, the contact openings including at least first and second arrays of test openings, characterized by different, respective first and second spacings between the test openings in the first and second arrays, the apparatus including:

a test station, which includes:

a particle beam source, which is adapted to direct a beam of charged particles to irradiate the test openings; and a current measuring device, which is coupled to measure, in response to the beam, at least one of a specimen current flowing through the first layer and a total yield of electrons emitted from a surface of the sample, thus producing an etch indicator signal; and a controller, which is adapted to analyze the etch indicator signal as a function of the spacings of the arrays of the test openings so as to assess a characteristic of the etch process.

There is furthermore provided, in accordance with an embodiment of the present invention, apparatus for monitoring a process carried out on a sample, the apparatus including:

a particle beam source, which is adapted to direct a beam of charged particles to irradiate the sample along a beam axis that deviates substantially in angle from a normal to a surface of the sample;

a current measuring device, which is coupled to measure, in response to the beam, a specimen current flowing through the sample; and a controller, which is adapted to analyze the specimen current so as to assess a characteristic of the etch process.

There is also provided, in accordance with an embodiment of the present invention, apparatus for process monitoring, including:

a particle beam source, which is adapted to direct a beam of charged particles to irradiate a surface of a sample, whereby electrons are emitted from the surface;

a bias electrode, which is adapted to apply an electric field in a vicinity of the surface, so as to cause at least a portion of the electrons emitted during the precharging interval to return to the surface, thereby generating a negative precharge at the surface; and a current measuring device, which is coupled to receive a signal produced by the sample in response to the beam and the negative precharge.

There is additionally provided, in accordance with an embodiment of the present invention, apparatus for testing a semiconductor device, including:

a radiation source, which is adapted to irradiate a junction in the semiconductor device with a first beam including electromagnetic radiation;

a particle beam source, which is adapted to irradiate the device with a second beam including charged particles, so that at least some of the charged particles are incident on the junction substantially simultaneously with the electromagnetic radiation; and a measuring element, which is adapted to measure, in response to incidence of the first and second beams on the junction, a property of the device.

There is further provided, in accordance with an embodiment of the present invention, apparatus for monitoring an etch process applied to a sample having a first layer that is at least partially conductive and a second layer formed over the first layer, following production of contact openings in the second layer by the etch process, the apparatus including:

a particle beam source, which is adapted to direct a beam of charged particles to irradiate one or more of the contact openings;

a beam current detector, for detecting a primary current of the beam;

a secondary electron detector, for detecting a total yield of electrons emitted from a surface of the sample in response incidence of the beam on the contact openings; and a controller, which is adapted a relation between the primary current and the total yield so as to assess a characteristic of the etch process.

There is moreover provided, in accordance with an embodiment of the present invention, apparatus for monitoring a process applied to a sample having a first layer that is at least partially conductive and a second layer formed over the first layer, contact openings having been created in the second layer by an etch process, the apparatus including:

a test station, including:

a particle beam source, which is adapted to direct a beam of charged particles to irradiate each of a plurality of the contact openings that are disposed at different, respective positions over a surface of the sample; and a current measuring device, which is adapted to produce an etch indicator signal by measuring, in response to irradiation of each of the plurality of the contact openings by the beam of charged particles, at least one of a specimen current flowing through the first layer and a total yield of electrons emitted from a surface of the sample; and a controller, which is adapted to store a calibrated threshold level of the etch indicator signal for a given set of properties of the etch process, and to compare the respective etch indicator signal produced with respect to each of the plurality of the contact openings to the threshold level so as to assess a characteristic of the etch process.

There is furthermore provided, in accordance with an embodiment of the present invention, apparatus for monitoring a process applied to a sample having a first layer that is at least partially conductive and a second layer formed over the first layer, contact openings having been formed in the second layer by an etch process, the apparatus including:

a test station, which includes:

a particle beam source, which is adapted to direct a beam of charged particles to irradiate each of a plurality of the openings that are disposed at different, respective positions across the sample; and a current measuring device, which is adapted to measure at least one of a specimen current flowing through the first layer and a total yield of electrons emitted from a surface of the sample in response to irradiation of the contact openings by the beam of charged particles, thus producing an etch indicator signal as a function of the respective positions of the plurality of the openings; and a controller, which is adapted to evaluate a variation of the etch indicator signal across the sample so as to assess a uniformity of the etch process.

There is also provided, in accordance with an embodiment of the present invention, a method for process monitoring of a sample having a first layer that is at least partially conductive, a second, barrier layer formed over the first layer, and a third, dielectric layer formed over the second layer, the method including:

etching contact openings in the third layer in a first etch process;

directing a beam of charged particles to irradiate the contact openings in a first monitoring step following the first etch process;

measuring at least one of a specimen current flowing through the first layer and a total yield of electrons emitted from a surface of the sample in response to irradiation of the contact openings by the beam of charged particles in the first monitoring step, thus producing a second etch indicator signal;

evaluating the first etch indicator signal to assess a first characteristic of the first etch process;

further etching the contact openings from the third layer into the second layer in a second etch process;

directing the beam of charged particles to irradiate the contact openings in a second monitoring step following the second etch process;

measuring the at least one of the specimen current flowing through the first layer and the total yield of the electrons emitted from the surface of the sample in response to irradiation of the contact openings by the beam of charged particles in the second monitoring step, thus producing a second etch indicator signal; and evaluating the second etch indicator signal to assess a second characteristic of the second etch process.

Typically, evaluating the first etch indicator signal includes assessing an integrity of the second layer.

Additionally or alternatively, evaluating the second etch indicator signal includes verifying that at least some of the contact openings have been etched through the second layer to the first layer.

There is additionally provided, in accordance with an embodiment of the present invention, apparatus for process monitoring of a sample having a first layer that is at least partially conductive, a second, barrier layer formed over the first layer, and a third, dielectric layer formed over the second layer, the apparatus including:

an etch station, which is adapted to form contact openings in the third layer in a first etch process, and subsequently to farther etch the contact openings from the third layer into the second layer in a second etch process;

a test station, which includes:

a particle beam source, which is adapted to direct a beam of charged particles to irradiate the contact openings; and a current measuring device, which is adapted to measure at least one of a specimen current flowing through the first layer and a total yield of electrons emitted from a surface of the sample in response to irradiation of the contact openings by the beam of charged particles, thus producing a first etch indicator signal following the first etch process and a second etch indicator signal following the second etch process; and a controller, which is adapted to evaluate the first etch indicator signal in order to assess a first characteristic of the first etch process and to evaluate the second etch indicator signal in order to assess a second characteristic of the second etch process.

BRIEF DESCRIPTION OF THE DRAWINGS

The present invention will be more fully understood from the following detailed description of the embodiments thereof, taken together with the drawings in which:

FIG. 1A is a schematic top view of a semiconductor wafer with a test pattern comprising an array of contact holes formed therein, in accordance with an embodiment of the present invention;

FIG. 1B is a schematic top view of another test pattern comprising sparse and dense arrays of contact holes, in accordance with an embodiment of the present invention;

FIGS. 2A-2E are schematic, sectional illustrations of an area of a semiconductor wafer, showing a contact hole etched into the wafer under different process conditions;

DETAILED DESCRIPTION OF EMBODIMENTS

System and Method Overview

Figure 1C:
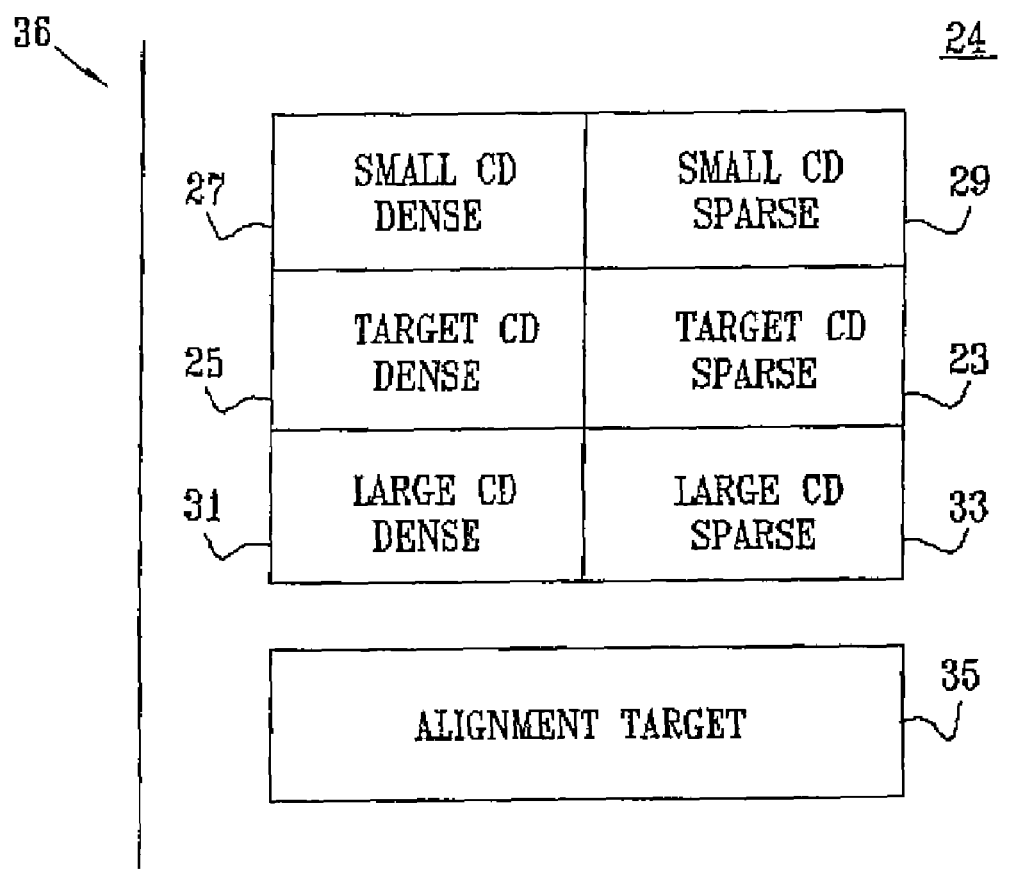
FIG. 1C is a schematic top view of a further test pattern comprising arrays of contact holes of different diameters and densities, in accordance with an embodiment of the present invention.

Reference is now made to FIG. 1A, which is a schematic top view of a semiconductor wafer 20 with a test pattern 22 formed thereon, in accordance with an embodiment of the present invention. The test pattern, comprising an array of contact holes 26, is shown enlarged in an inset. Although only the single test pattern 22 is shown in FIG. 1, multiple test patterns may be distributed over the surface of wafer 20. Other types of test openings and test patterns may also be used, such as the types described in the above-mentioned U.S. patent application Ser. No. 10/209,087. The test patterns may be located on scribe lines 24 between adjacent dice on wafer 20, so as to minimize the loss of useful space on the wafer. Additionally or alternatively, the methods of contact hole evaluation described hereinbelow may be applied, mutatis mutandis, to contact openings formed in functional areas of the dice.

Holes 26 in test pattern 22 may be graduated in diameter from large to small, as shown in the figure. The size gradation of the holes is particularly useful in assessing the state of an etch process used in processing wafer 20, as described below with reference to FIGS. 4 and 5. Typically, the holes are designed to range between 50 nm and 1 μm diameter and are spaced at least one diameter apart. These dimensions and spacing of the holes and of the test pattern are cited by way of example, however, and other dimensions and spacing may likewise be used. (The spacing between holes 26 may also be varied, as described below.) Although FIG. 1A shows a single row of holes 26, the holes may also be arranged in a two-dimensional pattern, and some of the holes may have the same diameter. The test pattern may also include other types of contact openings (not shown), such as trenches or vias.

FIG. 1B is a schematic top view of another test pattern 21, which may be formed on a semiconductor wafer, in accordance with an embodiment of the present invention. Pattern 21 comprises contact holes 26 arrayed in two patterns: a sparse pattern 23, and a dense pattern 25. Typically, holes 26 have the same diameter in both the sparse and dense patterns. As noted above, the etch rate of contact holes is typically lower in dense pattern 25 than in sparse pattern 23, due to micro-loading effects. The spacing of the contact holes in dense and sparse arrays in the test structure is typically chosen to represent limiting cases of actual contact hole spacing for in-die patterns. Therefore, by measuring specimen current through contact holes in the dense and sparse arrays, it is possible to detect etch problems that may occur within in-die patterns due to micro-loading.

FIG. 1C is a schematic top view of still another test pattern 36 within the area of a scribe line 24 on a semiconductor wafer, in accordance with an embodiment of the present invention. Pattern 36 combines the principles of the patterns shown above in FIGS. 1A and 1B. Pattern 36 comprises arrays 23 and 25 of sparse and dense contact holes, whose diameters are approximately equal to the critical dimension (CD) of the in-die functional contact holes that are produced on the wafer. In addition, the pattern comprises a dense array 27 and a sparse array 29 of contact holes having a smaller diameter than the in-die contact holes; and a dense array 31 and a sparse array 33 of contact holes having a larger diameter than the in-die contact holes. An alignment target 35 is typically provided in pattern 36 to facilitate optical alignment of an inspection system that is used to make specimen current measurements on the pattern, as described hereinbelow. Pattern 36 may also include an area that includes no contact holes, for use in establishing a calibration baseline for the specimen current measurements made on the pattern.

FIGS. 2A-2E are schematic, sectional illustrations of an area of a semiconductor wafer, showing formation of contact hole 26 under different process conditions. In a typical application, a non-conducting oxide layer 30 is formed over a silicon substrate layer 28, and photoresist (not shown in the figure) is deposited on the oxide layer. After photolithographic exposure of the photoresist to define the locations and dimensions of contact openings in the oxide layer, an etching process is applied to create the contact holes.

In the exemplary application shown in these figures, hole 26 is meant to provide a contact to a region 34 of substrate layer 28 that contains $TiSi_2$ for enhanced conductivity. Region 34 may be part of a transistor structure, formed within layer 28 by methods known in the art. Oxide layer 30 typically comprises materials such as undoped silicon glass (USG), phosphorus silicon glass (PSG), boron phosphorus silicon glass (BPSG), carbon-doped oxide (CDO) or low-k dielectrics. A barrier layer (not shown in this figure), sometimes referred to as an etch stop layer, which is typically made of silicon nitride, silicon carbide or a low-K barrier material, such as Applied Materials BLOk™, may be added between the silicon substrate and the dielectric. The structure illustrate in these figures, however, is shown solely by way of example, and holes 26 may likewise be made in and adjacent to other structures. Similarly, such contact holes may be used to contact intermediate semiconductor or conductive layers (not shown) formed above substrate 28, rather than contacting the substrate itself directly.

Holes 26 in test pattern 22 are formed by the same processes of material deposition, photolithography and etching as are the functional circuit features on the wafer that the pattern is intended to test. Within holes 26, substrate layer 28 is exposed to the same extent as it is exposed by etching of contact holes of similar diameter and spacing in functional areas of the wafer. A measurement of the specimen current generated when pattern 22 is irradiated by an electron beam is indicative of the extent to which layer 28 (or an overlying semiconductor or conductive layer) is exposed within the holes. To facilitate this measurement, a conductive contact pad (not shown in the figure) may be formed on the underside of wafer 20, below pattern 22. Apparatus and methods used in measuring the specimen current are shown in the figures that follow and are described with reference thereto.

FIG. 2A shows a perfectly-etched, open hole, i.e., a contact hole that cleanly exposes layer 28 as desired. The remaining figures in this set show the results of different process problems or defects. In FIG. 2B, hole 26 is underetched, typically due to a problem in the etching process or in the uniformity of oxide layer 30, for example. Consequently, the area of layer 28 that is exposed within hole 26 is smaller than it should be. In this case, the specimen current generated when the area of hole 26 is irradiated by an electron beam will be smaller than the current generated in the case of FIG. 2A. When the hole is filled with metal or other conductive material in order to contact layer 28, the contact resistance may be higher than it should.

In FIG. 2C, the etching process is too strong or has continued for too much time, leading to overetching of hole 26. In this case, the specimen current will typically be greater than in the case of FIG. 2A. Overetching may have a deleterious effect on region 34 and on other structures, and may also lead to deposit of contaminants at the bottom of hole 26.

FIG. 2D shows a case of severe underetching, in which hole 26 stops short of reaching layer 28, typically due to some serious process defect. For this sort of closed contact hole, the measured specimen current will be very low, and the contact resistance when the hole is filled with metal will be very high.

Finally, in FIG. 2E, although hole 26 was properly etched, a contaminant 38, such as photoresist residue or fluorocarbon polymer, is deposited at the bottom of the hole. This contaminant will typically cause a decrease in the measured specimen current. If the residue is not removed, it may cause a high contact resistance when hole 26 is filled with metal. This high contact resistance is a critical process problem, which can generally be detected (using methods known in the art) only many process steps later, after the metal layer has been deposited in the holes usually by electrical testing.

Figure 3A:
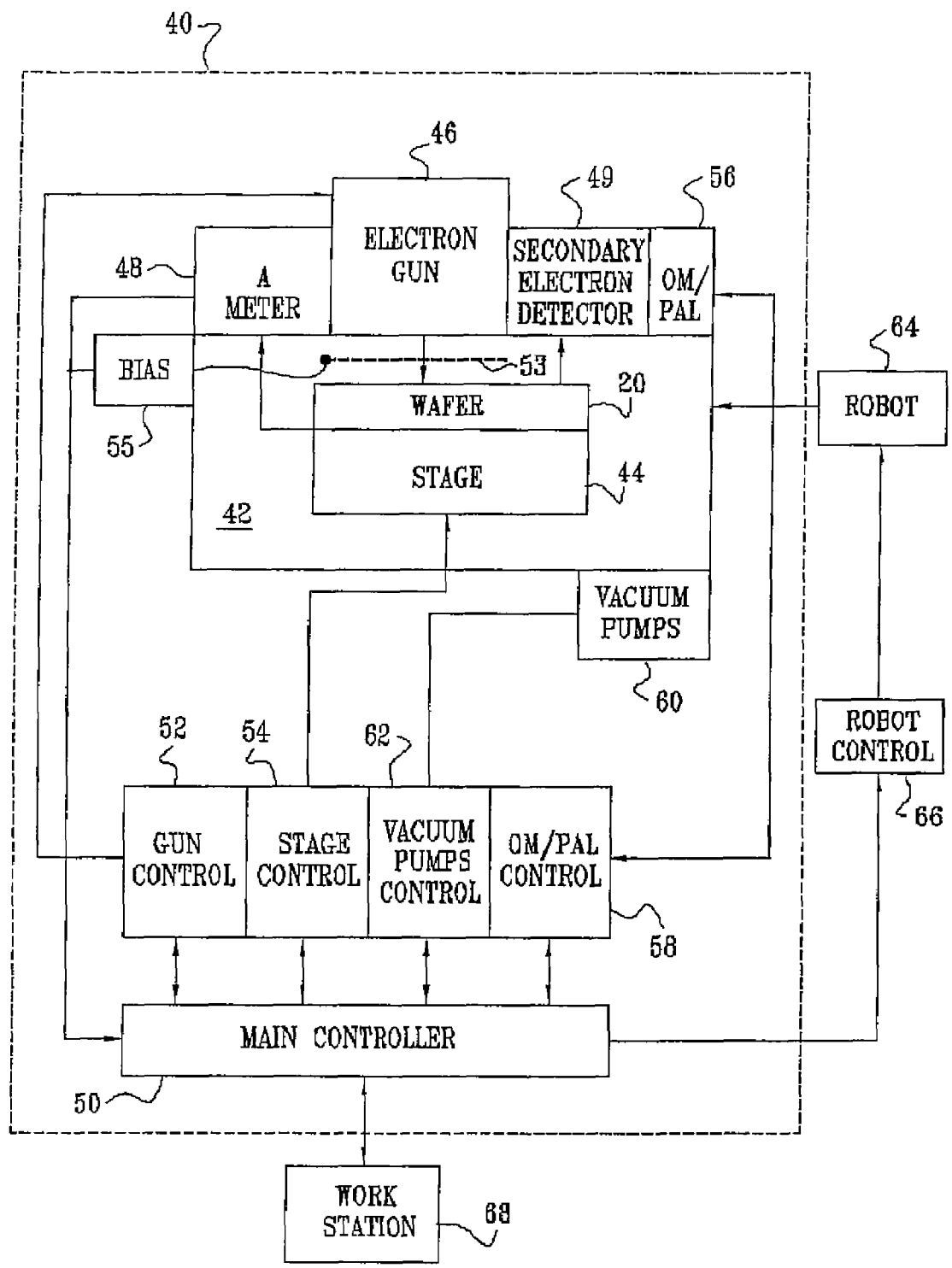
FIG. 3A is a block diagram that schematically illustrates apparatus for testing contact hole production, in accordance with an embodiment of the present invention.

FIG. 3A is a block diagram that schematically illustrates a station 40 for contact hole inspection, in accordance with an embodiment of the present invention. Station 40 comprises a chamber 42, containing a motion stage 44 on which wafer 20 is placed during inspection. An electron gun 46 (or other charged particle source) directs a beam at wafer 20, while an ammeter 48 measures the specimen current generated in the wafer. The ammeter is typically electrically coupled to the lower side of wafer 20, in electrical contact with substrate layer 28. Alternatively, the ammeter may be coupled directly to an intermediate semiconductor or conductive layer in the wafer, assuming that the layers on wafer 20 are suitably configured to enable such coupling. As noted above, the wafer may include one or more contact pads for use in coupling ammeter 48 to the substrate or intermediate layer.

The electron beam generated by gun 46 typically has a diameter and energy parameters that can be controlled as required by the application. The diameter may be adjusted to cover a single contact hole on the wafer, or expanded to irradiate several holes at once or to precharge the wafer surface. An adjustment range of 0.5-30 μm in beam diameter is generally adequate for these purposes. The electron energy of the gun may be variable, typically between about 100 and 5000 eV, so as to cover both positive and negative charging domains of the materials in wafer 20. (The positive charging domain is the range of electron energies in which the total yield of secondary and backscattered electrons from the surface layer is greater than the primary electron beam current, while the negative charging domain in the range in which the total yield is less than the primary beam current. These phenomena, which are well known in the art, are described in the above-mentioned book by Yacobi et al. on pages 38-39.) A suitable electron gun for this purpose, for example, is the EKF 1000 small-spot electron source, produced by Omicron NanoTechnology GmbH (Taunusstein, Germany). This gun is considerably smaller and less expensive than the high-resolution electron beam devices used in typical SEM systems. Alternatively, electron guns of other types, as well as other types of particle beams, may be used in station 40.

The specimen current due to irradiation of contact holes in wafer 20 is typically measured in steady state. For this purpose, the area of the contact hole to be irradiated is precharged by the beam from gun 46. This precharging may take place as a separate, preliminary stage, before making the specimen current measurements, or it may alternatively be carried out simultaneously with the measurements. The wafer surface may be negatively precharged, by operating the electron gun at an energy in the negative charging domain. For photoresist, this condition typically holds for all values of the electron beam energy. For $SiO_2$, a higher beam energy, preferably above 2 keV, can be used to give negative charging. Alternatively, a very low-energy beam can be used for negative charging.

Further alternatively, a bias electrode 53, which is negatively biased by a biasing power supply 55, may be used to induce negative charging by low-energy electrons. This application of the bias electrode is described below in detail with reference to FIG. 12. As yet a further alternative, negative charging of the surface may be achieved by applying an appropriate electric field bias to the wafer surface, using a charge control plate as described in U.S. patent application Ser. No. 08/892,734, filed Jul. 15, 1997, which is now U.S. Pat. No. 6,504,393, issued on Jan. 7, 2003, which is assigned to the assignee of the present patent application, and whose disclosure is incorporated herein by reference. In any case, negative precharging of the wafer surface causes holes 26 to act as Faraday cups, so that relatively few electrons escape from the holes.

Stage 44 positions wafer 20 so that each of contact holes 26 to be tested is properly located in turn in the beam of gun 46. Given the minimum diameter of the electron beam, positioning resolution of about ±3 μm is generally sufficient unless specific, individual contact holes are to be measured. For simplicity and economy of space, stage 44 may comprise an R-theta (translation/rotation) stage. Alternatively or additionally, any other type of motion system with sufficient accuracy may be used for this purpose. For example, the stage may provide X-Y translation, or gun 46 may be translated over wafer 20, or the electron beam itself may be deflected. When test holes or test patterns are provided on wafer 20 at multiple locations, stage 44 may position the wafer (or the electron gun may be translated or its beam deflected) so that several of these test holes or patterns are irradiated by the electron beam in succession. The specimen current is measured at each hole location, in order to ensure that contact hole uniformity is maintained over the entire wafer, as described further hereinbelow. Additionally or alternatively, if different test holes or test patterns on the wafer are designed to test different sizes or shapes of contact openings, the specimen current can be measured for each hole size or pattern type.

During the specimen current measurements, the beam energy of gun 46 is typically set to be in the negative charging domain of the top dielectric (background) layer, in order to provide optimal contrast between good, open contact holes and those that are closed or underetched. (As noted above, "open" contact holes are those that when filled with conductive material will be electrically conductive with low resistance; while holes that are closed, underetched or have residue remaining at the bottom may be electrically unconnected or exhibit high resistance when filled with the conductive material.) Typically, lower beam energy enhances the sensitivity of the measurement to thin layers of residual dielectric material at the bottom of the contact holes. Optionally, a number of different electron beam energies may be used to test the specimen current at a number of different points on the yield curve.

Figure 3B:
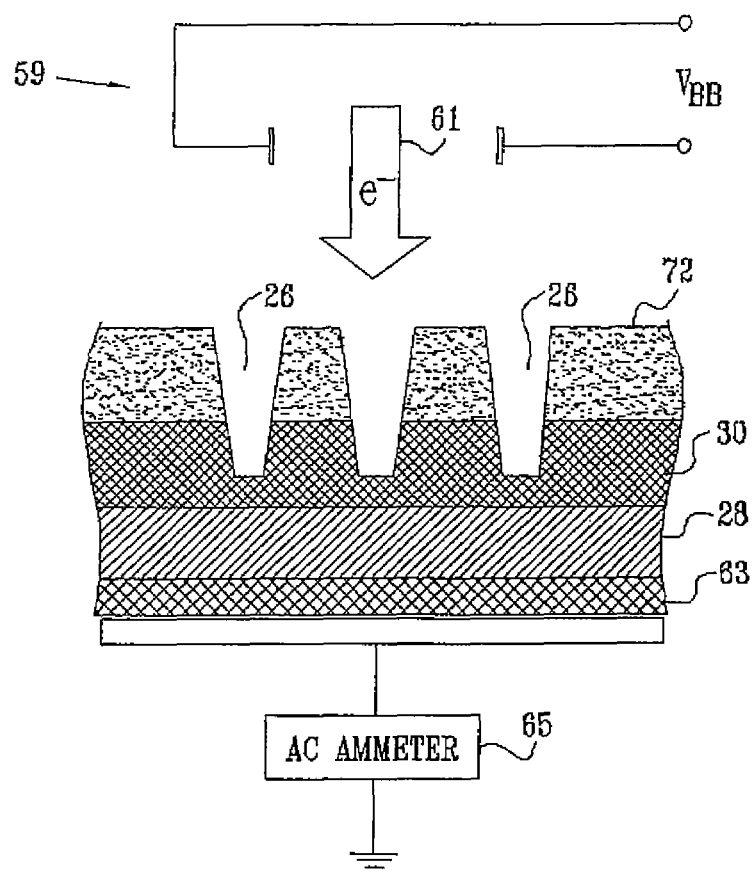
FIG. 3B is a schematic, sectional, detail view of a semiconductor wafer under test, illustrating periodic measurement of specimen current, in accordance with an embodiment of the present invention.
Figure 3C:
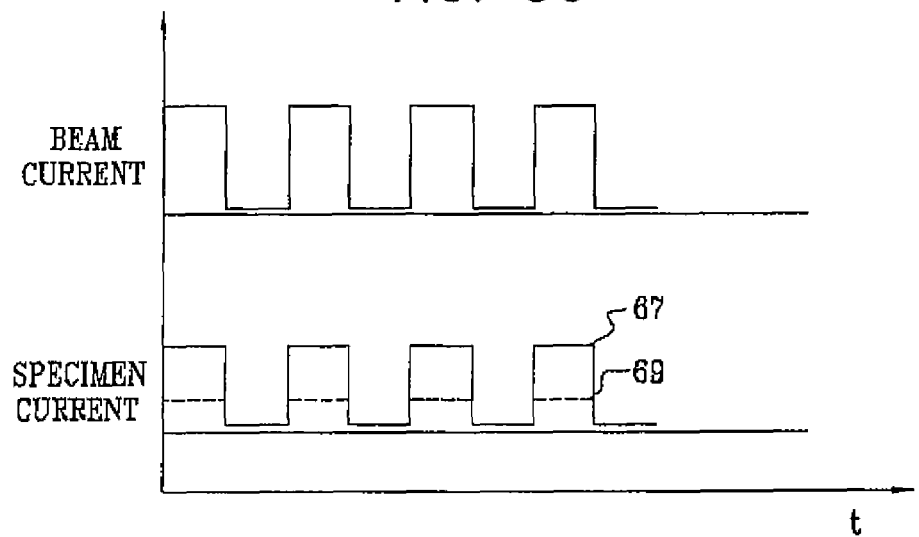
FIG. 3C is a schematic plot showing waveforms of an AC electron beam irradiating a semiconductor wafer and specimen current measured as a result of the irradiation, in accordance with an embodiment of the present invention.

FIGS. 3B and 3C illustrate an alternative method for measuring specimen current, in accordance with another embodiment of the present invention. If it is not possible to make a good ohmic contact between the semiconductor or conducting layer at the bottom of the contact holes and ammeter 48, the electron beam may be pulsed, and the specimen current measured by capacitive coupling. This arrangement is illustrated in FIG. 3B, which is a schematic, sectional view showing a detail of a wafer comprising substrate 28 and dielectric 30, with an additional back-side dielectric layer 63 below the semiconductor substrate. A photoresist layer 72 overlying dielectric layer 30 is used in creating contact holes 26. An electron beam 61 irradiates the area of contact holes 26. A beam blanking assembly 59 periodically applies a voltage $V_{BB}$ in order to pulse the electron beam on and off. The beam blanking assembly may comprise, for example, a pair of parallel metal plates, between which the electron beam travels before passing through an aperture. When a voltage is applied between the plates, the electron beam is deflected and does not pass through the aperture to reach the wafer. The resultant AC specimen current is measured using an AC ammeter 65, which is capacitively coupled to substrate 28 through dielectric layer 63.

FIG. 3C schematically shows the time variation of the electron beam current, which is tracked by the time variation of the specimen current. (Possible smoothing and phase shift of the specimen current waveform due to impedance effects are neglected here for the sake of simplicity.) An upper specimen current curve 67 illustrates the expected specimen current level when contact holes 26 are adequately etched. A lower specimen current curve 69 illustrates the reduction in specimen current that occurs due to etch problems, such as the underetching shown in FIG. 3B.

Alternatively, when a wafer under test has a back-side dielectric layer, the wafer may be mounted on a chuck with pins that contact the back side of the wafer. A pulsed voltage is applied to the pins in order to locally penetrate the dielectric layer and establish a good contact with substrate 28. The resistance between the pins may be measured in order to determine when sufficient penetration of the dielectric layer has been achieved.

Returning now to FIG. 3A, the current of electrons emitted from wafer 20 may be measured, additionally or alternatively, using a secondary electron detector 49, as is known in the art. As noted above, the specimen current generated in a sample due to irradiation by an electron beam is equal to the difference between the primary beam current and the total electron yield of the specimen due to secondary and backscattered electrons. Therefore, it is possible to determine the specimen current by measuring precisely the primary beam current and the total current of secondary and backscattered electrons, without measuring the specimen current itself directly. This approach typically requires collection of secondary and backscattered electrons high with efficiency—preferably >90%. This high efficiency can be achieved, for example, using a magnetic immersion lens, which forms at magnetic bottle at the surface of the specimen. Lenses of this sort are described in U.S. Pat. Nos. 4,864,228 and 4,912,405, whose disclosures are incorporated herein by reference. Alternatively, the secondary electron current may be used in conjunction with direct measurement of the specimen current in order to provide additional information that is complementary to the specimen current measurement.

The positioning and operation of gun 46 and stage 44 are controlled by a main controller 50, via a gun control unit 52 and a stage control unit 54. Typically, a pre-alignment unit based on a low-resolution optical microscope (OM/PAL) 56 is used by controller 50, via an OM/PAL control unit 58, to locate the test pattern on the wafer for positioning and alignment purposes. Suitable microscopes for this purpose are made, for example, by Optem (Fairport, N.Y.). During operation, a vacuum is maintained in chamber 42 by a vacuum pump 60, which is also controlled and monitored by controller 50, via a vacuum control unit 62. A robot 64 inserts wafers into chamber 42 and removes them from the chamber. Controller 50 communicates with the robot via a robot control unit 66. Robot 64 may be used to transfer wafers to and from other stations in a cluster tool, as shown below in FIG. 10.

After positioning stage 44 and firing gun 46 to irradiate one or more of contact holes 26, controller 50 receives the specimen current measured by ammeter 48. It compares the measured current to benchmarks that have been established for the expected hole size, materials, etch conditions and other applicable process parameters. Methods for determining these benchmarks are described hereinbelow with reference to the figures that follow. If the controller determines that the measured current is outside a predetermined tolerance range of a given benchmark, it typically interrupts the production process and notifies a system operator via a user workstation 68. The operator evaluates the test results and then implements whatever corrective action may be necessary.

The corrective action may include performing farther etching, if the contact holes are underetched (as shown in FIG. 2B or 2D), or removing polymer residue that may have been deposited at the bottoms of the holes (FIG. 2E). In the latter case, it may be possible to remove the polymer film by high-density electron beam exposure, using electron gun 46. For this purpose, electron beam energy between about 5 and 20 keV, with beam current greater than 1 nA, is expected to give satisfactory results. Thus, station 40 may be used for process correction, as well fault detection.

"Early Warning" Test Pattern

Figure 4:
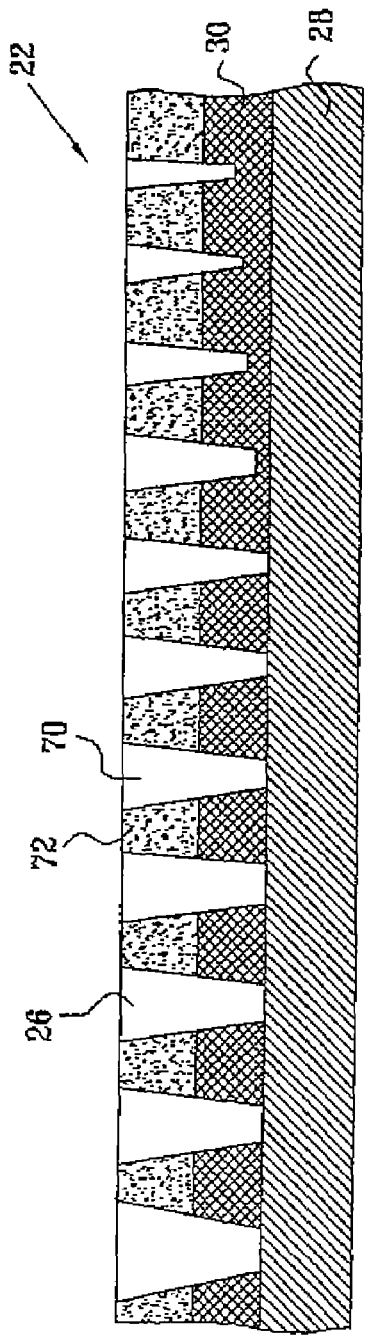
FIG. 4 is a schematic, sectional view of the array of contact holes in the test pattern of FIG. 1, taken along a line IV-IV.

FIG. 4 is a schematic, sectional view of test pattern 22 (FIG. 1), in accordance with an embodiment of the present invention. The test pattern is shown here following completion of an etching process. As noted above, the diameters of contact holes 26 in pattern 22 are graduated from largest (at the left of the figure) to smallest (at the right), ranged above and below the diameter of a nominal hole 70. The diameters of holes 26 are defined by a photolithographic process applied to photoresist layer 72, wherein nominal hole 70 is chosen to have approximately the same diameter as functional contact holes etched in functional areas of wafer 20.

The rate at which the etch process creates a contact hole increases as the contact hole diameter increases. Therefore, the etch state of nominal hole 70 should be approximately the same as that of functional contact holes in wafer 20. As shown in FIG. 4, upon satisfactory completion of the etch process, the holes of nominal diameter (i.e., the diameter of hole 70) and larger are etched through completely to substrate 28. Below the nominal diameter, the etching rate is slower, and therefore the depth of the holes decreases with decreasing hole diameter.

The situation shown in FIG. 4 is indicative of a properly-adjusted etch process, in that nominal hole 70 is fully etched through to the substrate, without overetching. There is a safety margin in the process (known as a "process window"), in that the contact holes in pattern 22 that are slightly narrower than the nominal hole are still etched through to the substrate (so that the nominal hole may be slightly overetched, but not to any deleterious extent). If still narrower holes were etched through to the substrate, there would be a danger of overetching the functional holes to which nominal hole 70 corresponds. On the other hand, if the holes just slightly narrower than nominal hole 70 were underetched (even if hole 70 still appears to be fully etched), there would be a danger of underetching the functional holes. Thus, monitoring the etching of test pattern 22 can provide an early warning of process defects, so that prompt corrective action can be taken. If these incipient defects were allowed to persist, they could result in improper etching of functional contact holes in the wafer under test or in other wafers processed subsequently in the same etching chamber as the current wafer.

Figure 5:
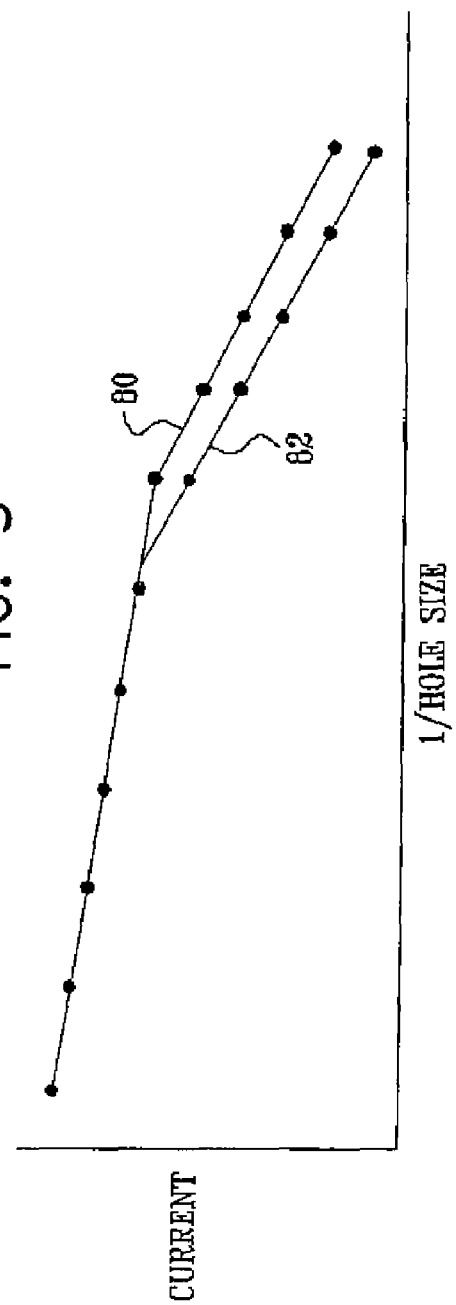
FIG. 5 is a schematic plot of specimen current as a function of hole size, for the array of contact holes shown in FIG. 4.

FIG. 5 is a schematic plot of specimen current as a function of the inverse of the hole diameter, measured with respect to test pattern 22 under two slightly different sets of etch conditions. Each data point in the plot corresponds to a measurement of specimen current made while irradiating one of holes 26 with an electron beam. (Typically, the spot size of the beam is larger than the hole diameter.) An upper curve 80 shows the specimen current measured for the set of hole depths shown in FIG. 4. The specimen current decreases gradually in proportion to the hole diameter down to a shoulder value, below which the current drops more sharply. This shoulder corresponds to the point at which the holes are no longer fully etched, leaving a highly-resistive dielectric layer at the bottom of the hole, with thickness increasing as hole diameter decreases. In curve 80, the shoulder occurs several points to the right of nominal hole 70, indicating that the etch process parameters are properly adjusted.

A lower curve 82 shows a change in the measured specimen current that may occur when the etch parameters drift from proper adjustment. The shoulder in curve 82 occurs closer to the point of nominal hole 70, although the specimen current measured through the nominal hole still indicates complete etching. In such a case, controller 50 may alert workstation 68 (FIG. 3) that a process deviation may be occurring, even though the etch state of the contact holes in the current wafer is still satisfactory. The operator can then correct the etch process before the deviation becomes severe enough to cause a reduction in the production yield.

Specimen Current Measurements and Threshold Calibration

Figure 6:
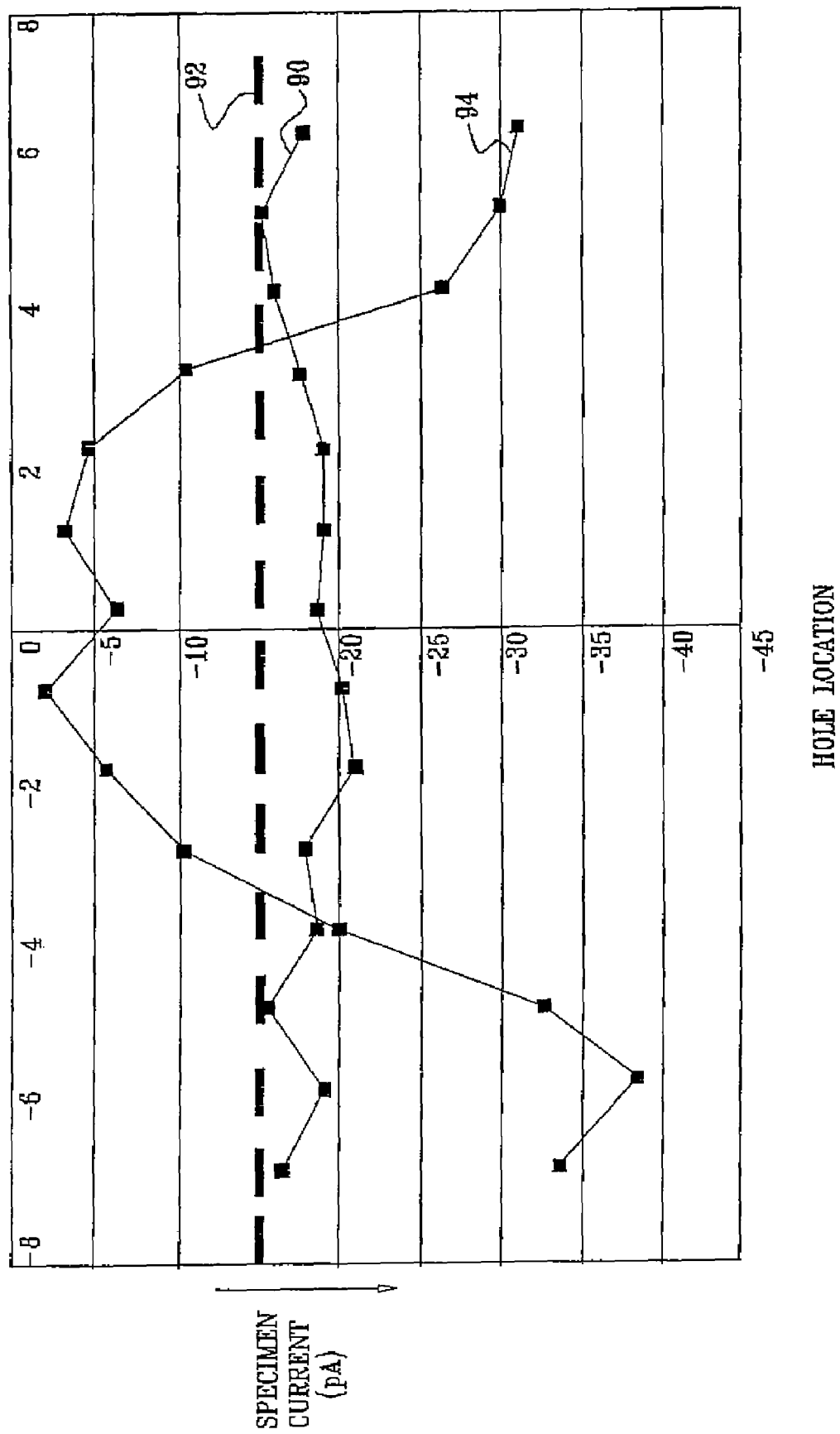
FIGS. 6-8 are schematic plots of specimen current measured as a function of contact hole position over the surface of a sample, in accordance with an embodiment of the present invention.
Figure 7:
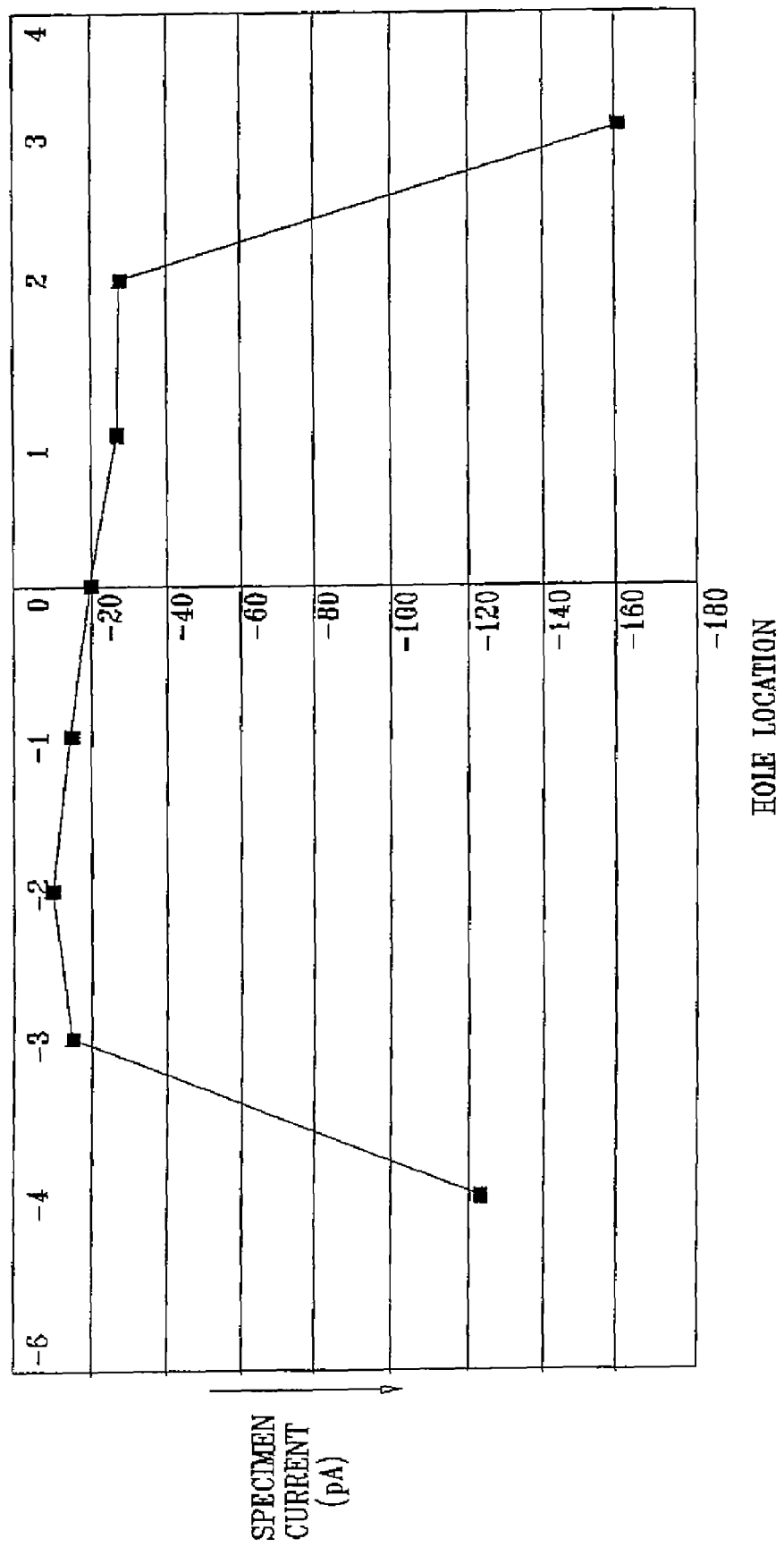
Figure 8:
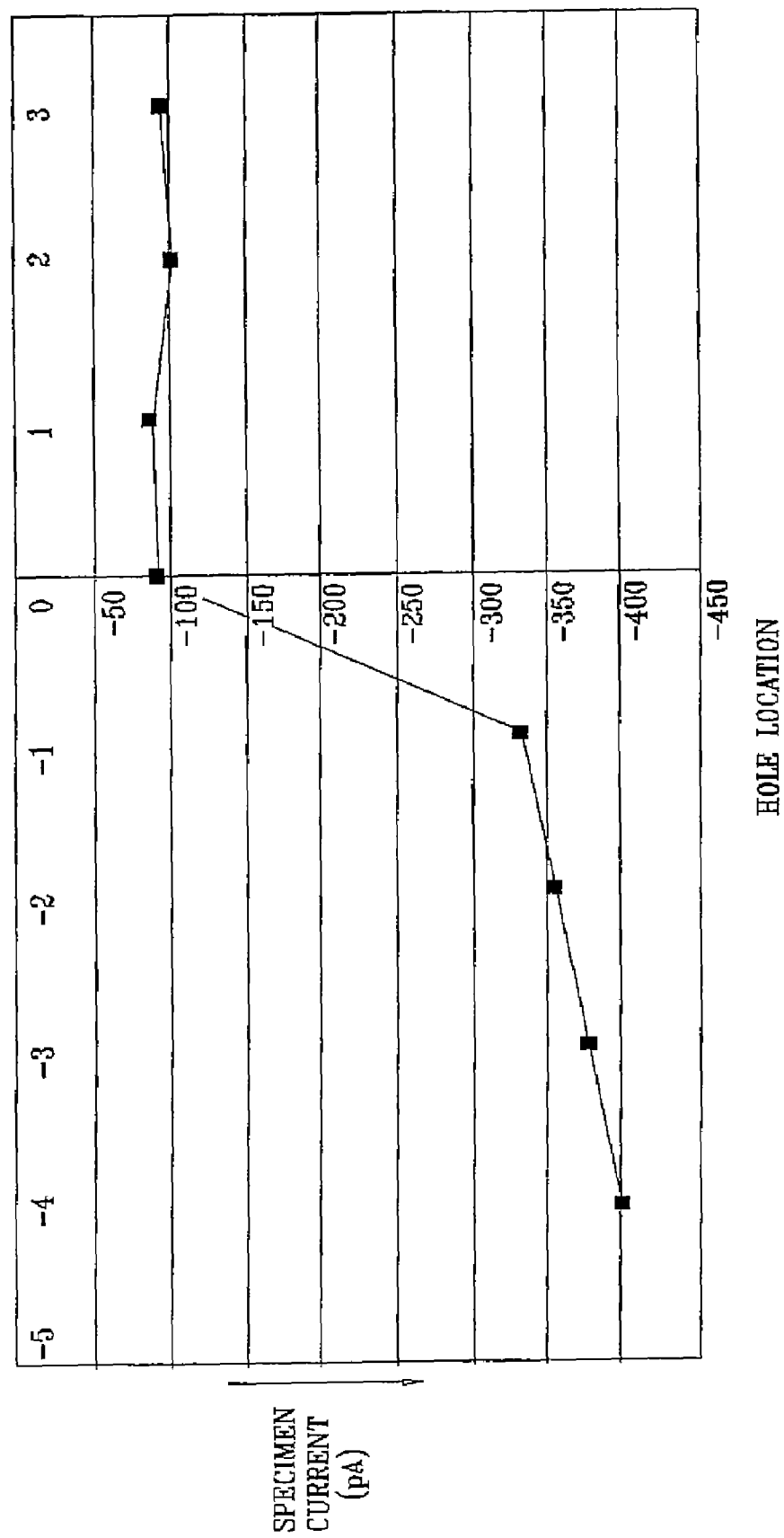

FIG. 6 is a plot of specimen current measured as a function of position across two test wafers using, for example, station 40 (FIG. 3), in accordance with an embodiment of the present invention. The vertical axis, representing the measured current in this figure and in FIGS. 7 and 8, is logically reversed, i.e., the measured current is negative, and the magnitude of the current increases from the top to the bottom of the plot. The measurements were made on contact holes at different locations along a diameter of the wafer, from one side of the wafer to the other. The contact holes were etched down to silicon substrate 28, without intervention of a nitride stop layer below oxide 30. The etch states of the holes were verified after measurement by cross-sectional imaging of the contact holes.

A first curve 90 was measured on a properly-etched wafer, in which the contact holes were etched for approximately 30% longer than nominal. Based on these measurements, it is possible to define a threshold 92, corresponding to satisfactory, normal etching of the wafer. The variation of the specimen current over the surface of the wafer may be used to define control limits, over which the specimen current is permitted to vary and still be considered within the acceptable range.

A second curve 94 was measured on a wafer of the same type as curve 90, which was etched using non-uniform process parameters. As a consequence, the contact holes in the central area of the wafer were underetched, resulting in low measured specimen current, while those on the periphery of the wafer were etched properly. Both these conditions are detected by station 40. A non-uniform profile, such as that of curve 94, is typically sufficient to indicate that a process problem exists and to notify a system operator or automatically stop processing wafers, even if the results are not above a specific absolute threshold.

The specimen current measurements shown in FIG. 6, as well as those shown in the figures that follow, were compared to cross-sectional images of the wafers that were tested, and a good correlation was found between the specimen current levels and the actual etch states of the contact holes.

FIG. 7 is a plot of specimen current measured as a function of position of contact holes distributed across another test wafer, in accordance with an embodiment of the present invention. In this case, the wafer included a nitride stop layer below the oxide that was etched. The low specimen current measured upon irradiation of the central points in the curve is indicative of underetching of the holes at these points. Toward the edges of the wafer, the holes were fully etched, down to the nitride layer. Because of the relatively high conductivity of silicon nitride, relative to silicon (which may have been enhanced by the electron beam irradiation), the specimen current flowing through these holes is considerably greater than that shown in FIG. 6.

FIG. 8 is a plot of specimen current measured as a function of position of contact holes distributed across yet another test wafer, in accordance with an embodiment of the present invention. This figure illustrates the capability of station 40 to detect residues in etching of the nitride etch stop layer (which is typically performed as a separate process step, to remove the barrier layer from the bottom of contact holes, after first etching the hole through the overlying oxide). The nitride layer was etched out of the contact holes on one side of the wafer, shown to the left in the plot of FIG. 8, but was left intact on the other side. It can be seen from this figure that the methods of the present invention may be used to monitor not only the state of an oxide etching process, but also other etching processes, including nitride etching.

FIGS. 7 and 8 thus demonstrate that the methods of the present invention may be used to monitor etching of dual dielectric layers (upper dielectric with stop layer below). Etch stop layers are now used in many applications, particularly high aspect ratio contact and via processes in devices such as DRAM. The dual dielectric layers are typically etched in two different, successive etch steps, one for each layer. It is important that the first etch step, illustrated by FIG. 7, reaches but does not punch through the stop layer. Punch-through may occur, for example, due to low selectivity in the first etch step or to use of a very thin stop layer. The punch-through would be evidenced by an abnormally large value of the specimen current upon conclusion of the first etch step, while underetching in the first etch step gives low specimen current, as shown in FIG. 7. The second etch step, in which the contact holes are etched through the stop layer may be monitored in similar fashion, but with different threshold levels to indicate proper etching.

Figure 9A:
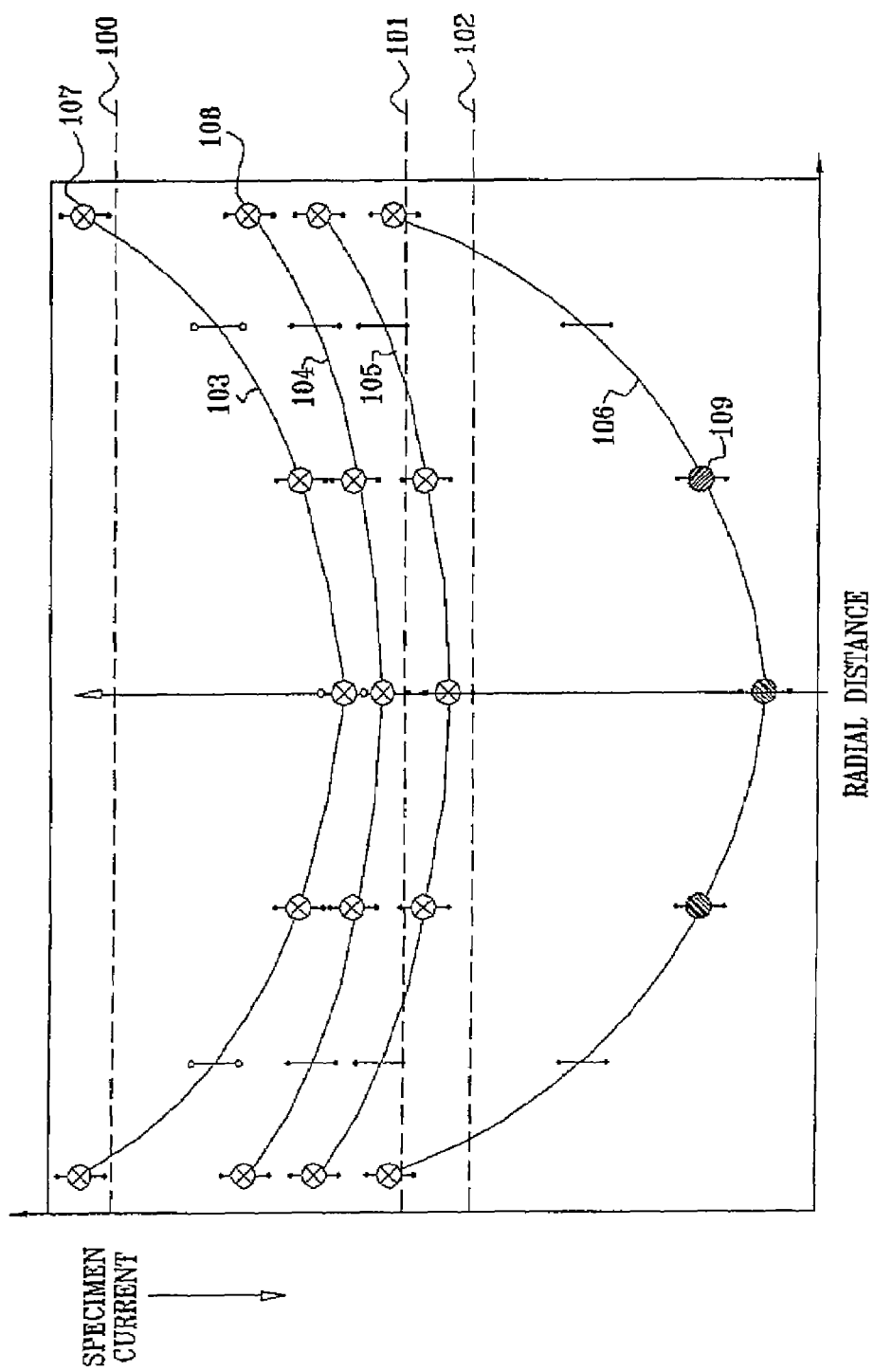
FIGS. 9A and 9B are schematic plots of specimen current measured as a function of contact hole position over the surface of a sample, illustrating calibration thresholds used in contact hole monitoring, in accordance with an embodiment of the present invention.

FIG. 9A shows schematic plots 103, 104, 105 and 106 of specimen current (absolute values), measured as a function of contact hole position for a number of different samples. The measured currents are used in calibrating absolute process control limits, in accordance with an embodiment of the present invention. Plots 103-106 are measured using test structures and measurement methods such as those described above. The measurements of specimen current from specific contact holes are compared to cross-sectional images of the same contact holes. Some or all of the dies used in the specimen current measurements may be sectioned for this purpose. These measurements are then used in establishing an upper excursion limit 100 and a lower excursion limit 102, marking the bounds of measured specimen current values 108 that correspond to acceptable contact holes.

Plot 106 illustrates specimen current measurement values 109 that were made on an underetched wafer. In this case, only the contact holes on the wafer periphery were adequately etched. (Whether the peripheral holes are etched differently from those nearer the center of the wafer depends on factors such as the etcher type, process recipe and materials, inter alia.)

Plot 105 was taken from a slightly overetched wafer, and demonstrates properly-etched contact holes over the entire wafer diameter. Proper etching of the contact holes is verified by cross-sectional imaging. Plot 105 can be used to establish lower excursion limit 102, based on the minimal absolute value of the specimen current on this plot, taking the estimated measurement error (illustrated by the error bars in the figure) into consideration. If the cross-sectional images show any of the holes on this wafer to be underetched, on the other hand, another wafer may be etched, using a longer etch time, and may be tested in like manner to establish the lower excursion limit.

Plot 104 illustrates specimen current measurements made on a wafer etched according to an optimized method, in accordance with an embodiment of the present invention, which typically corresponds to extending the etching time by 10-30% compared to that used in generating plot 105. The minimal specimen current measurement on plot 106 is used in determining a lower control limit (LCL) 101, again taking into account the estimated measurement error. When the calibration bounds determined by the present method are used in monitoring production wafers, and the measured specimen current drops below LCL 101, an early warning signal may be issued to warn of possible process drift. Typically, the specimen current measurements from a number of wafers may be analyzed statistically in order to set LCL 101, so as to account for normal etch process variations.

Plot 103 shows specimen current measurements taken from a strongly-overetched wafer. In this case, measurement values 107 are indicative of punch-through of a stop layer below the main dielectric layer being etched, as described above. The punch-through is verified by cross-sectional images. Upper excursion limit 100 is set to correspond to the maximal specimen current value below the error bounds of measurements 107.

Figure 9B:
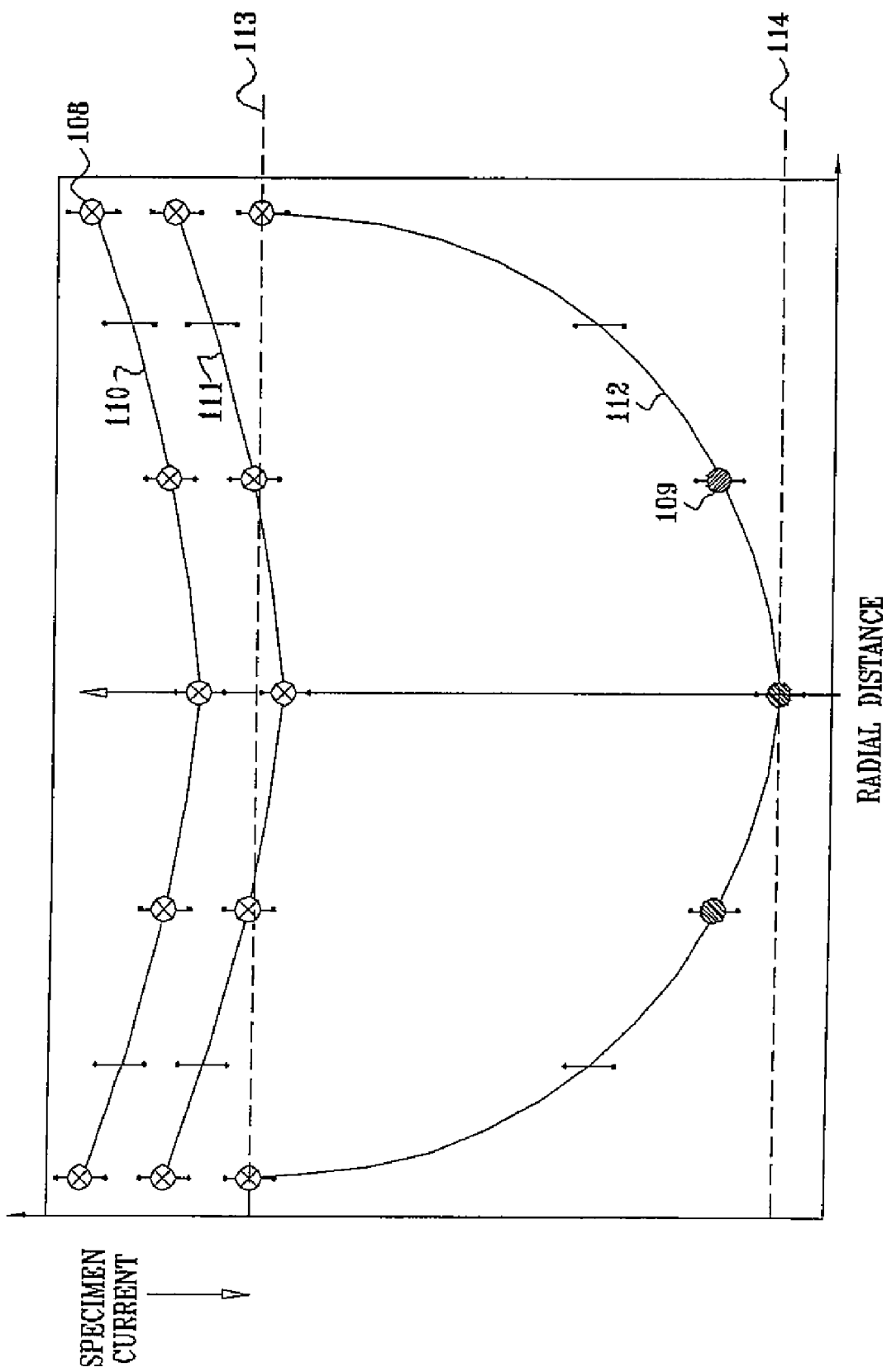

FIG. 9B schematically illustrates specimen current measurements used in calibrating relative control limits, in accordance with an embodiment of the present invention. The inventors have found that underetched wafers tend to exhibit very high non-uniformity of specimen current measurements taken across the wafer diameter. As shown in FIG. 9B, the non-uniformity in a plot 112 taken on an underetched wafer may reach 100%, as indicated by a maximum current value 113 and a minimum current value 114 reached by this plot. By contrast, plots 110 and 111 show that for properly-etched wafers, the non-uniformity is typically no more than 10-15%. Non-uniformity is also significant in overetched wafers in which punch-through has occurred.

The relative control limit for non-uniformity is thus a single value, indicating the maximal permitted variation among specimen current measurements taken over the diameter of a wafer. It can be determined from plot 111, for example, which shows the measurements made on a slightly-overetched wafer, as verified by cross-sectional imaging. The relative control limit is typically applied in subsequent measurements on production wafers as an average non-uniformity value (including error bars). Excursions of the average non-uniformity above the relative control limit are considered to indicate underetching or punch-through in the contact holes on the wafer under test. The use of such a relative control limit is advantageous in that it provides fast, reliable process monitoring, which is insensitive to variations in the specimen current due to drift in the primary electron beam current.

Alternatively or additionally, the primary electron beam current may be monitored, and the ratio of the specimen current to the primary beam current may be used as an etch quality indicator.

Figure 10:
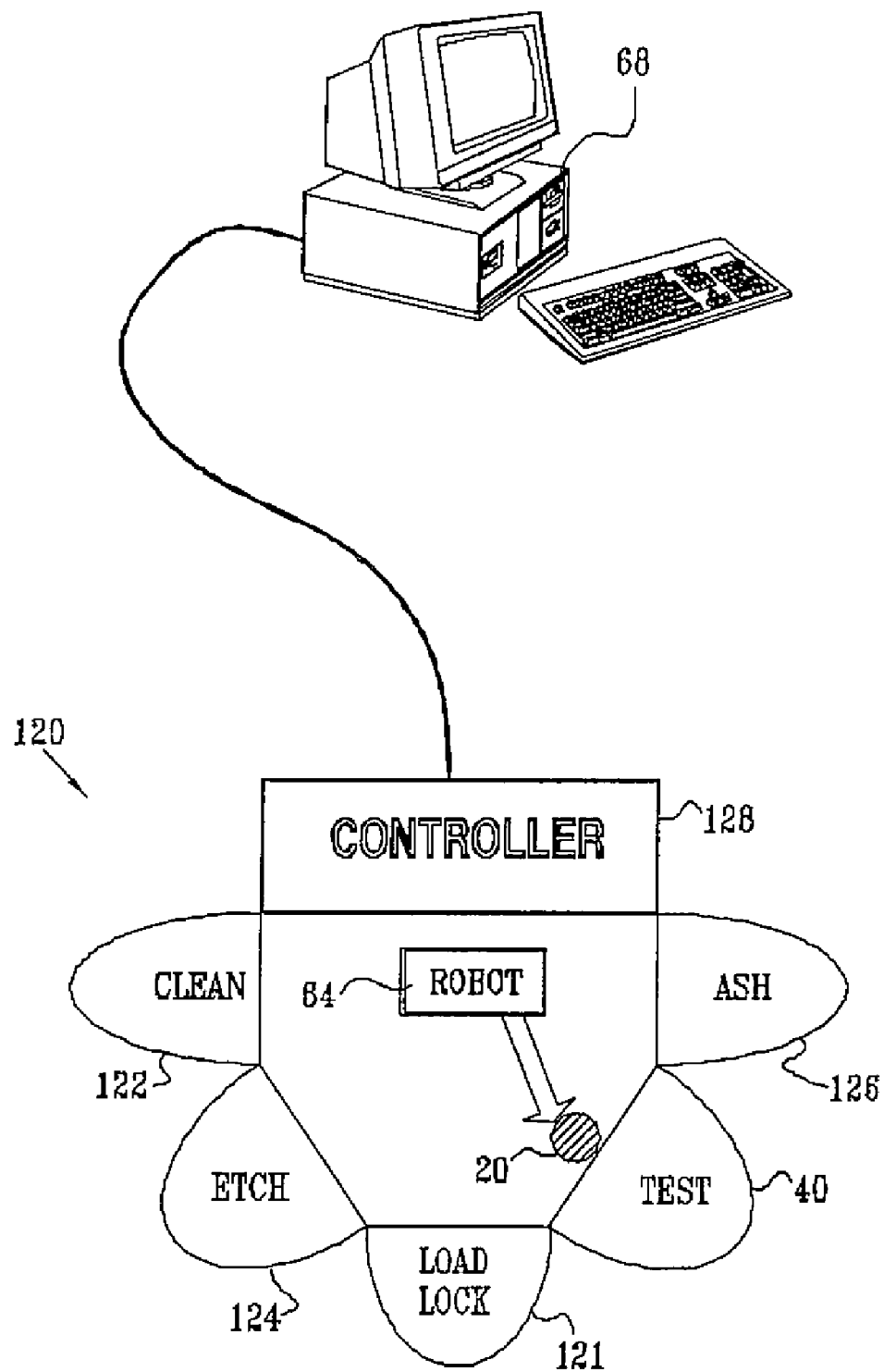
FIG. 10 is a schematic top view of a cluster tool that includes a contact hole test station, in accordance with an embodiment of the present invention.

FIG. 10 is a schematic top view of an etch process cluster tool 120 in which test station 40 is integrated, in accordance with an embodiment of the present invention. This integration is made possible by the small size and simplicity of the components of station 40. Robot 64 receives wafer 20 through a load lock 21, after photoresist has been deposited over oxide layer 30 and has then been exposed by photolithography to form circuit features including contacts and/or vias, with a suitable test pattern, such as pattern 22. Since the interior of tool 120 is evacuated, robot 64 is able to transfer wafer 20 from chamber to chamber without exposing the wafer to ambient air. Typically, the wafer is inserted in an etching station 124. At this stage, holes 26 are formed through layer 30, preferably by a reactive ion etching process. The foregoing steps are known in the art and are described here solely by way of illustration. Other arrangements of the stations in tool 120 may similarly be used.

After etching of holes 26 in wafer 20, the wafer is passed to test station 40. At this point, the wafer (except for the etched holes) is still covered by a layer of exposed photoresist. In station 40, the specimen current from wafer 20 is measured at one or more pre-defined points, either in product dies or on test structures or both. The results are evaluated, as described above, by a controller 128 (which may incorporate the functions of controller 50, shown in FIG. 3). Typically, the controller evaluates the specimen current for multiple holes distributed across the wafer, as shown in the preceding figures, and compares the measured values to both absolute and relative thresholds for the process in question. If the specimen current for all holes measured is within the tolerance range defined by the thresholds, the contact holes in the wafer are deemed to be acceptable. Robot 64 then moves wafer 20 into a plasma ashing station 126 for removal of the remaining photoresist, and to a cleaning station 122. If desired, the contact hole test in chamber 40 may be repeated after the ashing stage.

On the other hand, if the specimen current measured in station 40 is too low, indicating that the holes have been underetched, robot 64 may be instructed (automatically or manually) to return the wafer to etching station 74 for further etching, to be followed by re-test in station 40. Under these circumstances, controller 128 typically issues an alarm to workstation 68, as well, indicating to the operator that an adjustment of process parameters may be needed. Alternatively, controller 128 may autonomously adjust certain process parameters (increasing or decreasing the etch duration in etching station 124, for example), in response to deviations of the specimen current from ideal behavior.

Contact Hole Measurements Using an Angle E-Beam

Figure 11:
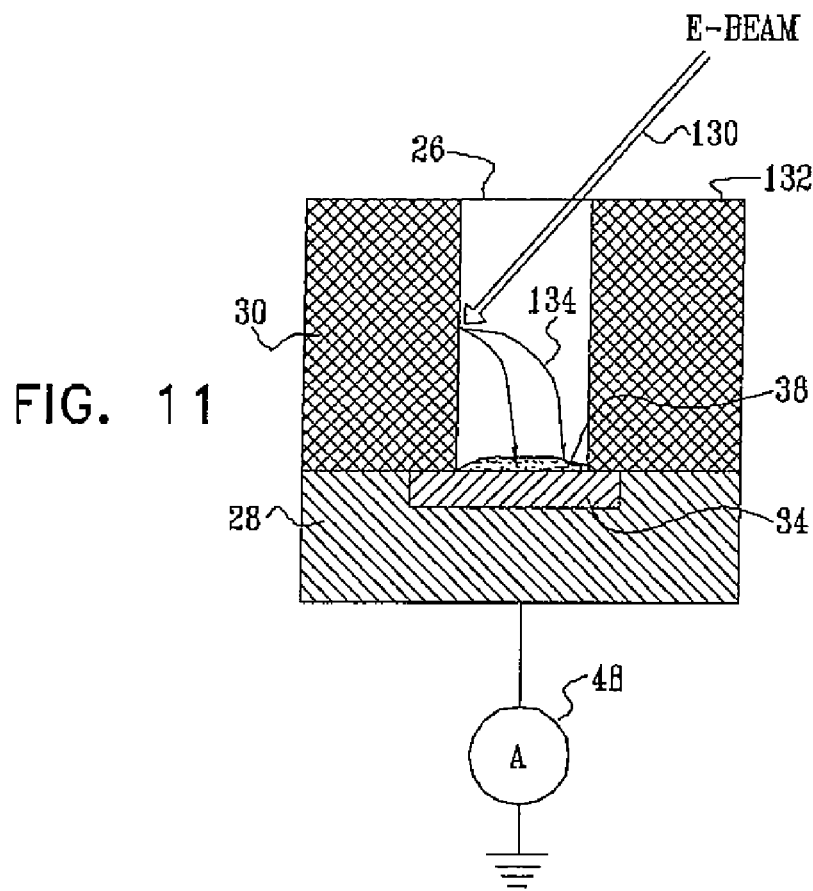
FIG. 11 is a schematic, sectional view of a contact hole on which an electron beam is incident at a non-normal angle, in accordance with an embodiment of the present invention.

FIG. 11 is a schematic, sectional illustration showing angled irradiation of contact hole 26 by an electron beam 130, in accordance with an embodiment of the present invention. The tilt angle of beam 130 is preferably chosen so that a majority of primary beam electrons do not strike the bottom of the contact hole. This condition can be achieved when the following geometrical condition is satisfied:

$$\alpha > \arctan(1/AR),$$

wherein $\alpha$ is the tilt angle, and AR is the aspect ratio (ratio of depth to diameter) of the contact hole.

As a result of the tilt angle, the primary electrons hit the side wall of the hole 26 rather than the bottom. The electron bombardment causes emission of secondary electrons with low energy (typically <50 eV). The low-energy secondary electrons can be forced down to the hole bottom, rather than moving out of the hole, by negatively precharging a surface 132 of the wafer around the hole. If the contact hole is etched properly (with no residue left at the bottom), the low-energy electron flow will pass through substrate 28 and will thus be measured as a specimen current by ammeter 48. If a thin residue (even tens of Angstroms thick), such as under etched dielectric or contaminant 38, is left after the etch, the specimen current will be much lower, due to low penetration depth of the low-energy secondary electrons.

Similar results may be achieved using a very low energy (preferably 50-500 eV) primary electron beam at normal incidence. The lower energy in either case reduces the interaction volume at the surface of the bottom of the hole and thus substantially increases the sensitivity of the specimen current to thin layers.

By contrast, when electron beam 130 operates at higher energy and is not angled, the energetic primary electrons reach the bottom of hole 26. In this case, the interaction volume is larger, and the electrons thus pass easily through contaminant 38. Therefore, holes with particularly thin residues cannot be readily distinguished from holes that have been etched satisfactorily. Angling electron beam 130 thus provides an electron energy transformation inside hole 26, which substantially enhances sensitivity of the specimen current measurement to very thin residues at the hole bottom. This method is particularly useful in detecting fluorocarbon polymer residue, organic photoresist residue, and extremely thin oxide, nitride or other dielectric residue (including low-k dielectric with a corresponding stop layer). It can be performed by station 40 in-line, providing closed-loop monitoring of reactive ion (plasma) etching, photoresist ashing, and wet polymer cleaning steps.

Tilting of electron beam 130 may be achieved by either mechanical means or by the use of electron optics to control the beam, or by a combination of both techniques. Some CD SEM systems, such as the Applied Materials NanoSEM3D, provide this sort of beam tilt capability.

Negative Precharging Using a Bias Electrode

As noted above, it is desirable in specimen current measurements for contact hole monitoring to negatively precharge surface 132 of wafer 20. In order to induce a negative precharge on oxide layer 30 using primary electron beam 130, it is typically necessary to work at a beam energy of several keV (up to 5 keV depending on the dielectric type). Such high energy electrons, however, can damage silicide layers and gate oxides in the wafer, which may lead to semiconductor device degradation, failure or yield loss.

Figure 12:
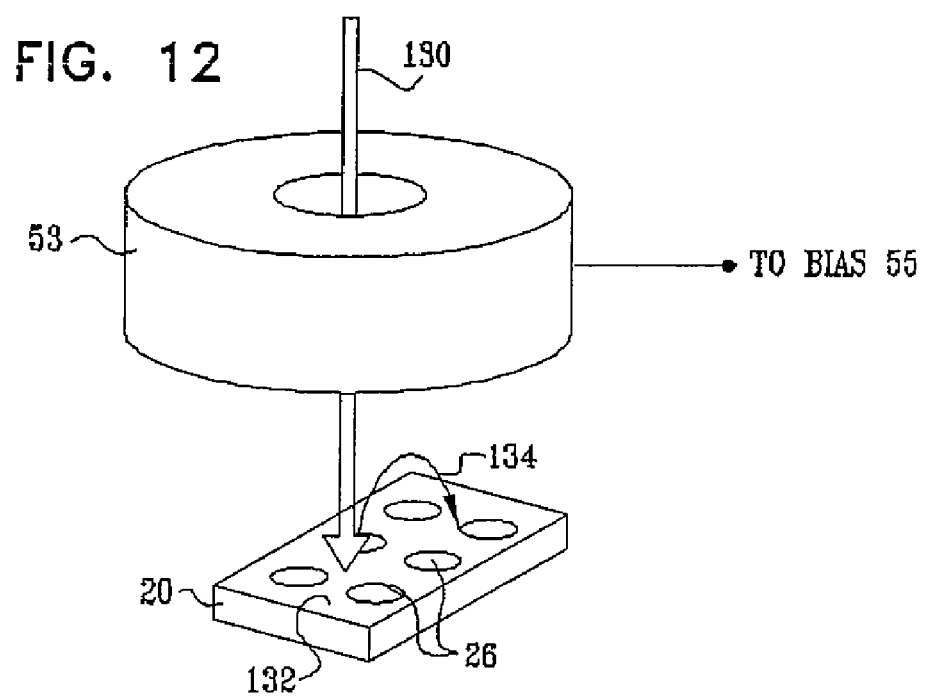
FIG. 12 is a schematic, pictorial illustration of a biasing electrode used in conjunction with an electron beam to pre-charge a surface of a sample, in accordance with an embodiment of the present invention.

FIG. 12 is a schematic, pictorial illustration, showing how bias electrode 53 may be used to alleviate this problem, in accordance with an embodiment of the present invention. In this figure, electrode is shown as a ring, with an aperture for beam 130. Alternatively, electrode 53 may comprise a fine grid, for example, or may be produced in other, as will be apparent to those skilled in the art. The use of a biased filter mesh of this sort—albeit for other purposes—is described in European Patent Application EP 0 892 275 A2, whose disclosure is incorporated herein by reference. It is even possible to adapt the bottom electrode (i.e., the electrode next to wafer 20) of a SEM immersion lens to serve this purpose.

Electrode 53 is negatively biased by power supply 55. The negative bias repels secondary electrons 134 that are emitted from surface 132 due to incidence of beam 130, without substantially influencing the primary electron energy of beam 130. By repelling the low-energy secondary electrons back to surface 132, electrode 53 creating a negative net charge on the dielectric surface. In other words, electrode 53 causes the total electron charge leaving the surface to be less than the charge acquired by the surface due to the primary electron irradiation. The inventors have found that using a 1 keV primary electron beam with a −50 V bias on electrode 53 provides satisfactory precharging of surface 132. Electrode 53 was about 1 cm in diameter and was placed about 1.5 mm from surface 132. The electrode had a central aperture about 1 mm in diameter through which beam 130 passed. This method of precharging may be used advantageously in conjunction with the angled beam irradiation method shown in FIG. 11.

Combined Optical and E-Beam Excitation

Figure 13:
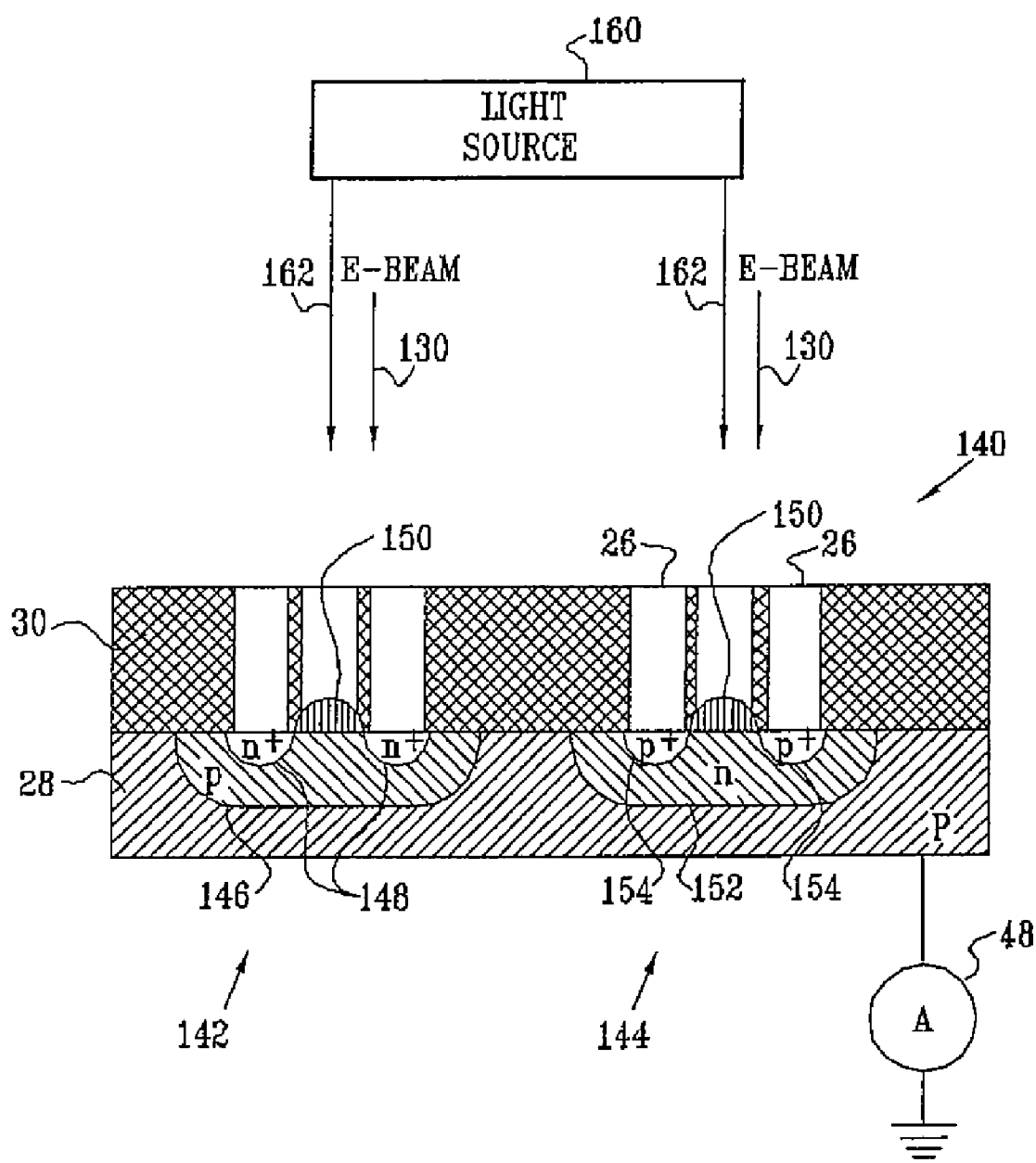
FIG. 13 is a schematic, sectional illustration showing simultaneous irradiation of a sample by electron and light beams, and measurement of the resultant specimen current, in accordance with an embodiment of the present invention.

FIG. 13 schematically illustrates an active transistor structure 140, which is irradiated simultaneously by e-beam 130 and by an optical beam 162 produced by a light source 160, in accordance with another embodiment of the present invention. This embodiment is directed particularly to etch quality assessment of functional contact holes, used in producing microelectronic devices on wafer 20.

Structure 140 is a typical CMOS structure, which includes an NMOS transistor 142 and a PMOS transistor 144. As is known in the art, transistor 142 is situated in a P-well 146, containing N-type source/drain 148 and a gate 150, while transistor 144 is situated in an N-well 152 with P-type source/drain 154 and its own gate 150. If contact holes 26 are irradiated by electron beam 130 alone, the P-N-P structure of PMOS transistor 144 will present a very high resistance to any specimen current that is generated, regardless of external bias. Therefore, it becomes difficult to make accurate measurements of the quality of contact holes 26 based on the specimen current.

To solve this problem, light source 160 irradiates structure 140 with beam 162, which typically comprises visible, near infrared or ultraviolet light. The photon energy of beam 162 is chosen so that absorption of the beam causes electron-hole pairs to be generated within the P-N junctions of transistors 142 and 144, as well as in PIN wells and the bulk silicon of substrate 28. In silicon, for example, the frequency of beam 162 is typically chosen to give photon energy in the vicinity of the bandgap (about 1.12 eV) or above. The presence of the photoelectrons substantially increases the conductivity of PMOS transistor 144, so that the specimen current upon irradiation by electron beam 130 can be readily measured. The photoelectrons may also enhance the measurement of specimen current from NMOS transistor 142, if the natural conductivity due to negatively-charged dielectric 130 is insufficient.

Other applications of combined electromagnetic and charged particle irradiation in semiconductor wafer inspection will be apparent to those skilled in the art. For example, when electromagnetic energy is applied during SEM imaging, the contrast properties of circuit features may be altered, thereby providing additional image information that would not otherwise be present.

Although the embodiments described hereinabove are directed particularly to contact hole monitoring, the principles of the present invention may also be applied to other quality control tasks, such as measurement and monitoring of other feature dimensions (particularly critical dimensions) in the semiconductor wafer fabrication process. The methods of the present invention provide an indication both of the width of such features and of the thickness of layers making up the features. These methods can be adapted for use not only before metal deposition, as in the embodiments described above, but also after metal deposition to inspect contacts, interconnects and metal lines for disconnects, short circuits and other defects.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for process monitoring, comprising:
   directing a beam of charged particles to irradiate a surface of a sample, the sample having a first layer that is at least partially conductive and a second layer formed over the first layer, whereby electrons are emitted from the surface;
   applying an electric field in a vicinity of the surface, so as to cause at least a portion of the emitted electrons to return to the surface, thereby generating a negative precharge at a surface of the second layer; and
   receiving a signal produced by the sample in response to the beam and the negative precharge,
   wherein the sample has contact openings formed in the second layer by an etch process, and wherein receiving the signal comprises analyzing the signal so as to assess a characteristic of the etch process.

2. The method according to claim 1, wherein the second layer comprises a dielectric material.

3. The method according to claim 1, wherein receiving the signal comprises measuring at least one of a specimen current flowing through the sample and a total yield of electrons emitted from the surface of the sample.

4. The method according to claim 1, wherein the sample comprises a semiconductor wafer, and wherein the contact openings comprise at least one of contact holes, trenches and vias.

5. The method according to claim 1, wherein the sample has a barrier layer formed between the first and second layers, and wherein analyzing the signal comprises analyzing the signal after etching the second layer in order to assess an integrity of the barrier layer, and then analyzing the signal after etching the barrier layer.

6. The method according to claim 1, wherein directing the beam comprises operating the beam during a precharging interval so as to generate the negative precharge at the surface, and then operating the beam after the precharging interval so as to generate the signal.

7. The method according to claim 6, wherein operating the beam during the precharging interval comprises configuring a beam source so that electrons from the beam have an energy in a positive charging domain of the surface of the sample.

8. Apparatus for process monitoring, comprising:
a particle beam source adapted to direct a beam of charged particles to irradiate a surface of a sample, whereby electrons are emitted from the surface;
a bias electrode adapted to apply an electric field in a vicinity of the surface, so as to cause at least a portion of the electrons emitted during a precharging interval to return to the surface, thereby generating a negative precharge at the surface; and
a current measuring device adapted to measuring a specimen current flowing through the sample, the specimen current produced in response to the beam and the negative precharge.

9. The apparatus according to claim 8, wherein the sample has a first layer that is at least partially conductive and a second layer formed over the first layer, and wherein the bias electrode is further adapted to cause at least a portion of electrons emitted during the recharging interval to return to a surface of the second layer, thereby generating a negative precharge at the surface of the second layer.

10. The apparatus according to claim 8, wherein the current measuring device is further adapted to measure a total yield of electrons emitted from the surface of the sample.

11. The apparatus according to claim 8, wherein the sample has a first layer that is at least partially conductive and a second layer formed over the first layer, with contact openings formed in the second layer by an etch process, and wherein the current measuring device is further adapted to produce a signal indicative of a characteristic of the etch process.

12. The apparatus according to claim 8, wherein the sample comprises a semiconductor wafer, and wherein the current measuring device is further adapted to produce a signal indicative of a characteristic of at least one of contact holes, trenches and vias.

13. The apparatus according to claim 8, wherein the sample has a barrier layer formed over a first layer and a second layer formed over the barrier layer, and wherein the current measuring device is further adapted, after etching of the second layer, to measure a first signal indicative of an integrity of the barrier layer, and the current measuring device is further adapted, after etching of the barrier layer, to measure a second signal indicative of an extent to which contact openings have been etched through the barrier layer to the first layer.

14. The apparatus according to claim 8, wherein the beam source is adjustable to produce the beam with first beam characteristics during the precharging interval so as to generate the negative precharge at the surface, and then to produce the beam after the precharging interval with second beam characteristics, so as to generate the specimen current.

15. The apparatus according to claim 14, wherein the beam source is adapted to irradiate, during the precharging interval, the surface with charged particles having an energy in a positive charging domain of the surface of the sample.

* * * * *